United States Patent [19]

Reeves et al.

[11] Patent Number: 5,538,425
[45] Date of Patent: Jul. 23, 1996

[54] DENTAL HANDPIECE WITH DISPOSABLE DRILL HEAD ASSEMBLY

[76] Inventors: Gloria Reeves, 2625 Country Creek La., Fort Worth, Tex. 76123; Mary Burdette, 8508 Woodlake Cir., Fort Worth, Tex. 76179; Jerry Reeves, 2625 Country Creek La., Fort Worth, Tex. 76123; Ian Floyd, 8508 Woodlake Cir., Fort Worth, Tex. 76179

[21] Appl. No.: 311,416

[22] Filed: Sep. 23, 1994

Related U.S. Application Data

[63] Continuation of Ser. No. 242,189, May 13, 1994, abandoned, which is a continuation-in-part of Ser. No. 128,891, Sep. 30, 1993, abandoned, which is a continuation-in-part of Ser. No. 928,815, Aug. 13, 1992, abandoned.

[51] Int. Cl.$^6$ ............................................. A61C 1/10
[52] U.S. Cl. .......................... 433/82; 433/126; 433/132
[58] Field of Search ................................ 433/82, 84, 85, 433/126, 132

[56] References Cited

U.S. PATENT DOCUMENTS

| | | | |
|---|---|---|---|
| Re. 24,391 | 11/1957 | McFadden | 433/132 |
| 3,014,278 | 12/1961 | Aymar et al. | 433/132 |
| 3,120,705 | 2/1964 | Hoffmeister et al. | 433/132 |
| 3,252,719 | 5/1966 | Borden | 433/132 |
| 3,418,715 | 12/1968 | Ellis | 433/132 |
| 3,955,284 | 5/1976 | Balson | 433/132 |
| 4,403,956 | 9/1983 | Nakanishi | 433/82 |
| 4,477,252 | 10/1984 | Lieb et al. | 433/126 |
| 4,614,498 | 9/1986 | Vaccaro | 433/126 |
| 5,252,067 | 10/1993 | Kakimoto | 433/132 |
| 5,308,242 | 5/1994 | McLaughlin et al. | 433/126 |

FOREIGN PATENT DOCUMENTS

| 371552 | 10/1963 | Switzerland | 433/132 |
|---|---|---|---|

*Primary Examiner*—Cary E. O'Connor
*Attorney, Agent, or Firm*—Arthur F. Zobal

[57] ABSTRACT

The dental handpiece includes a disposable head assembly and a reusable handle which are removably coupled together. The head assembly includes a housing formed of plastic material forming a cavity in which is located a turbine operated drill assembly with a drill burr extending out of a lower opening. The upper wall of the housing is formed against the top of the drill assembly to permanently fix the drill assembly in the cavity such that the bearing mechanism for rotatably supporting the turbine and drill burr is integral with the head assembly. The head assembly also has a neck with a cavity for removably receiving the proboscis of the handle by way of a rear opening. The handle supplies and removes air to and from the head cavity for operating the turbine and also supplies air, water and light from the proboscis which are directed toward the burr by way of an outlet opening. The handle is snap-locked to the head assembly when the proboscis is located in the neck cavity. A protuberance extends from the proboscis for snap-locking the handle and the head assembly together. The lock mechanism of the head assembly may be broken away to remove the head assembly from the handle after which the head can be discarded.

28 Claims, 20 Drawing Sheets

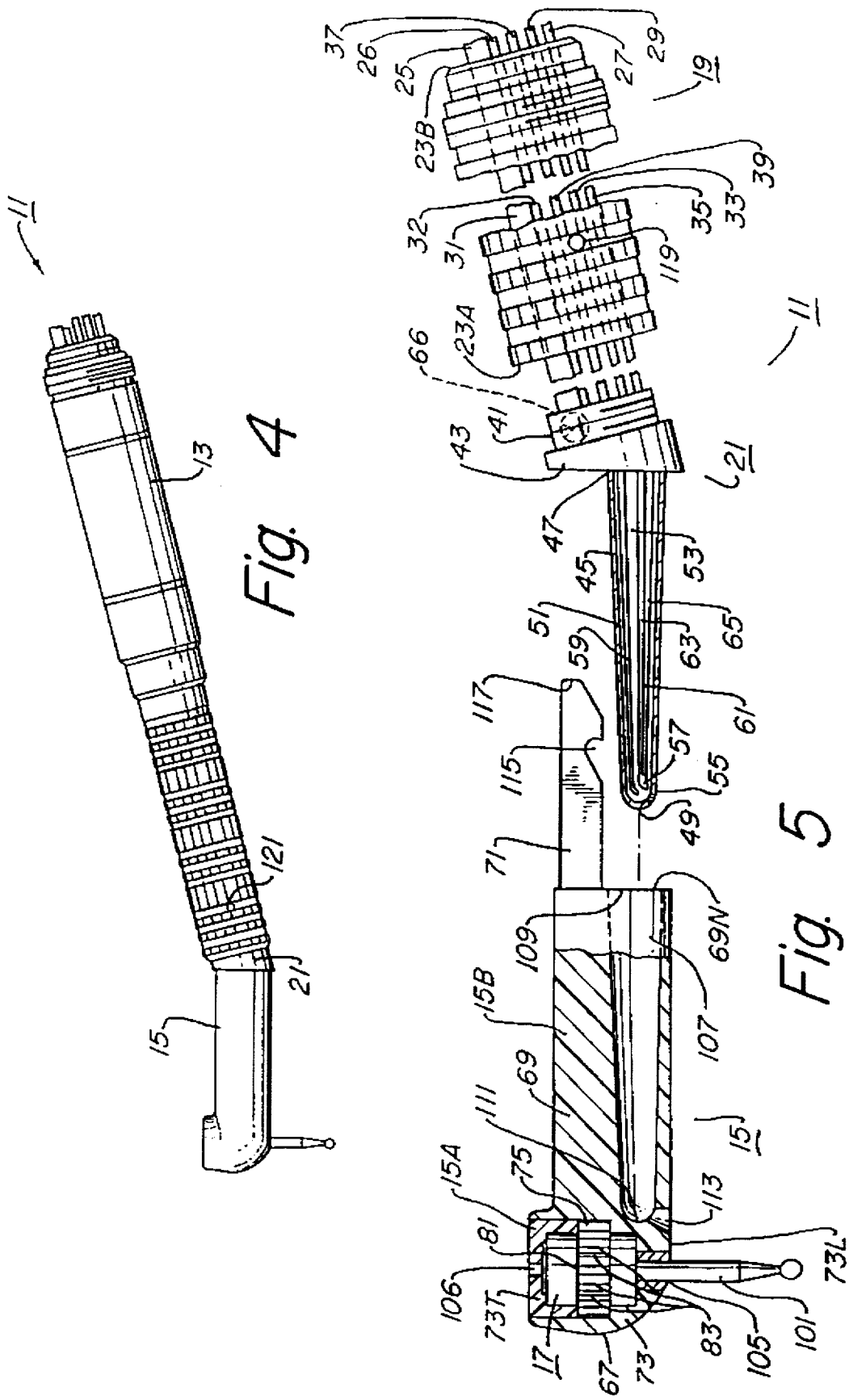

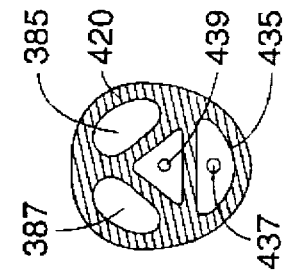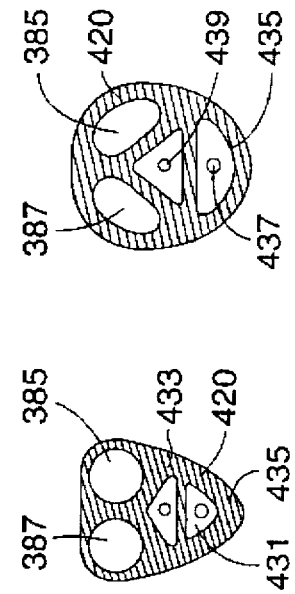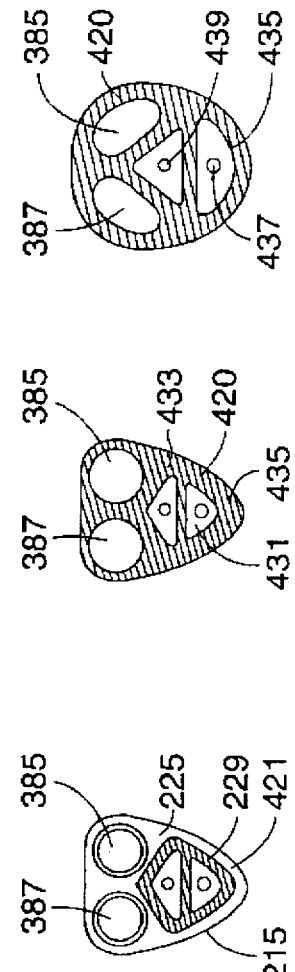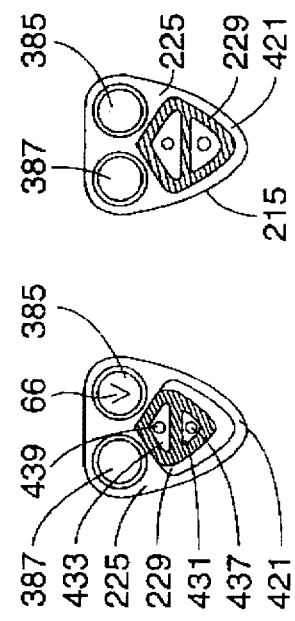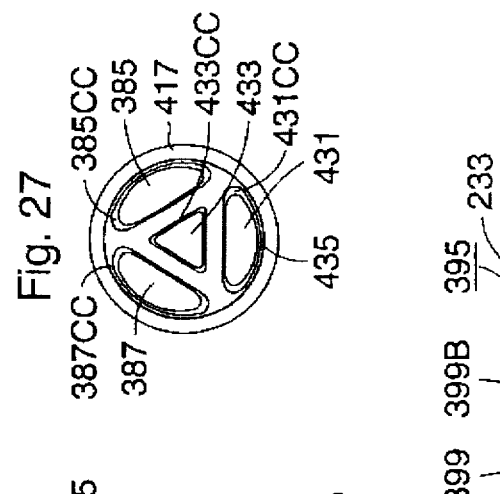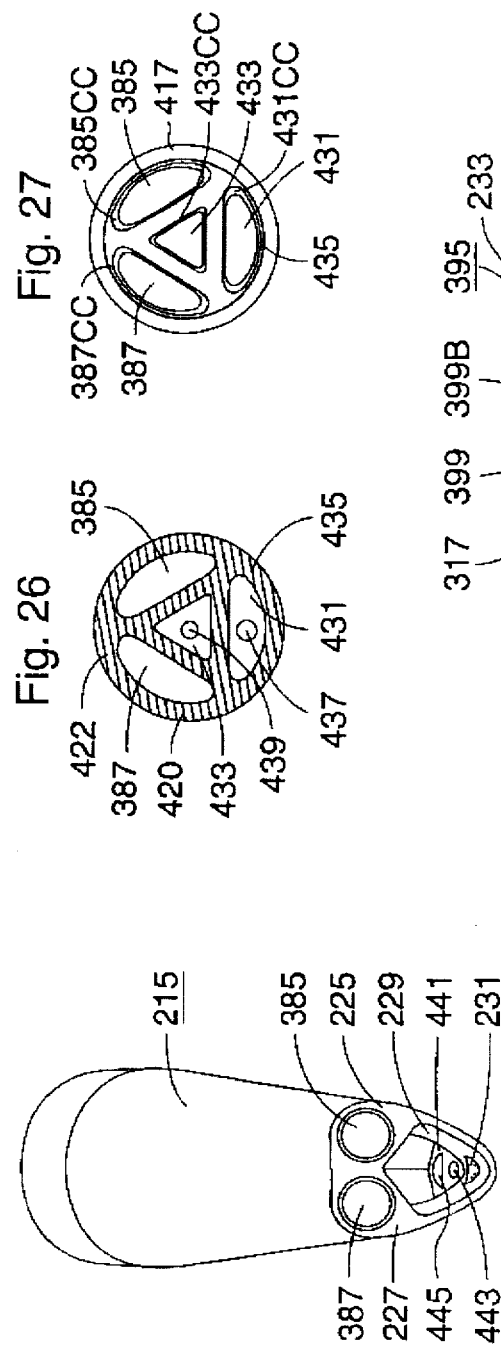

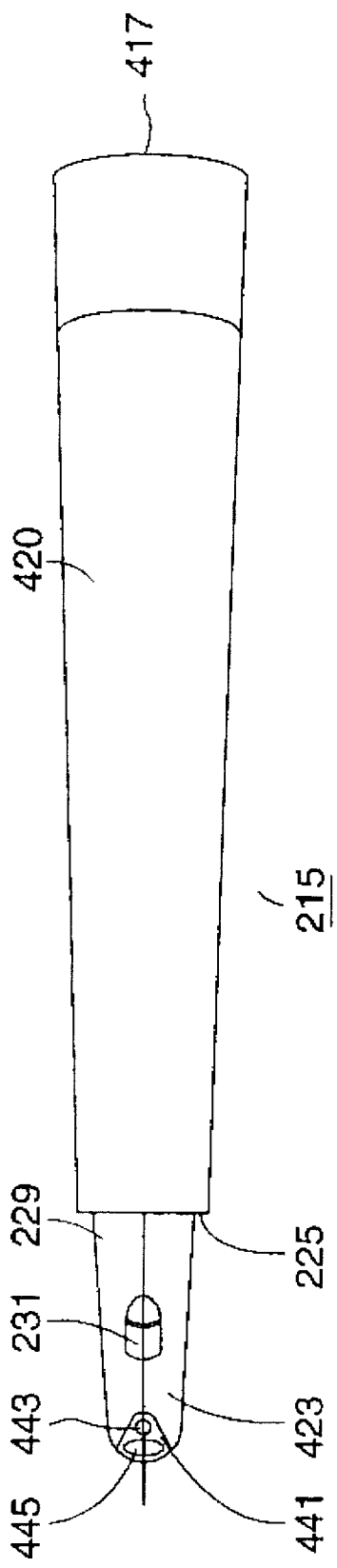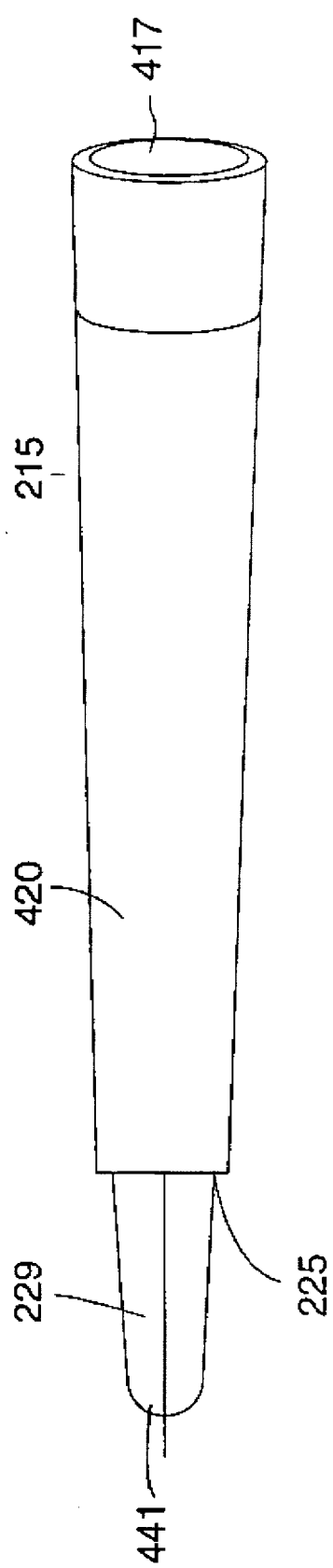

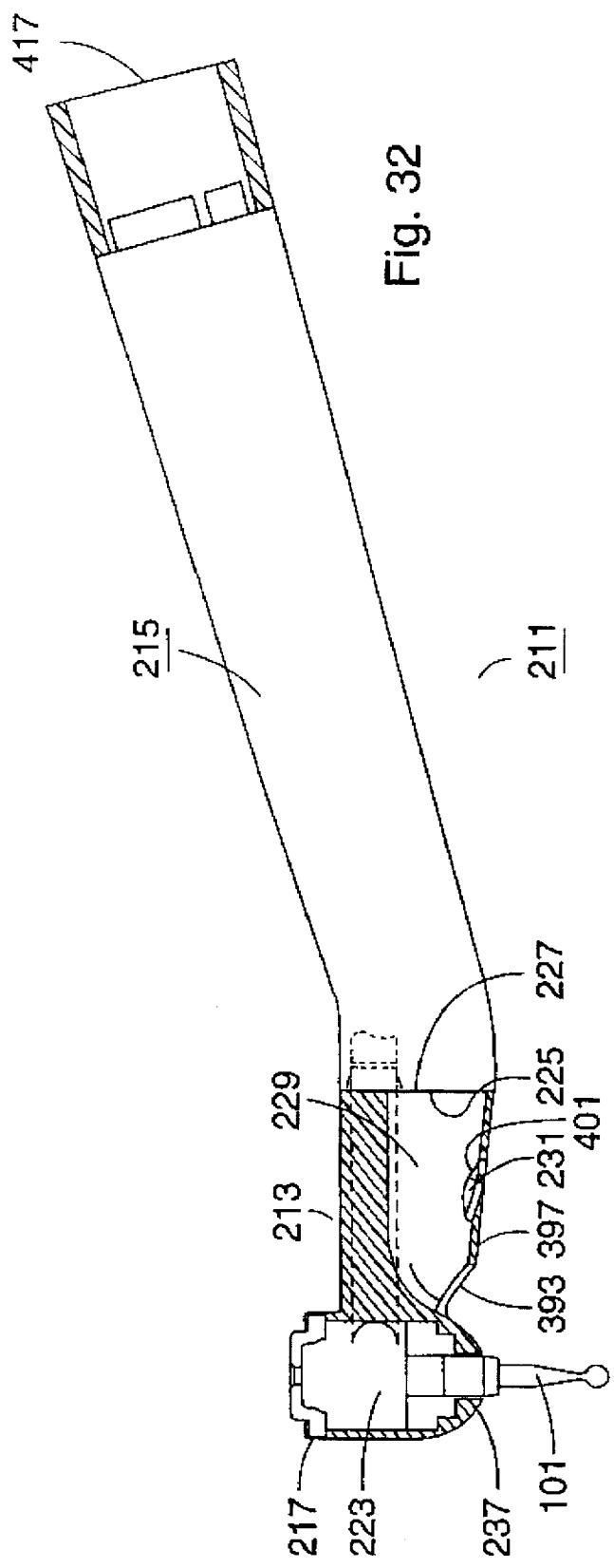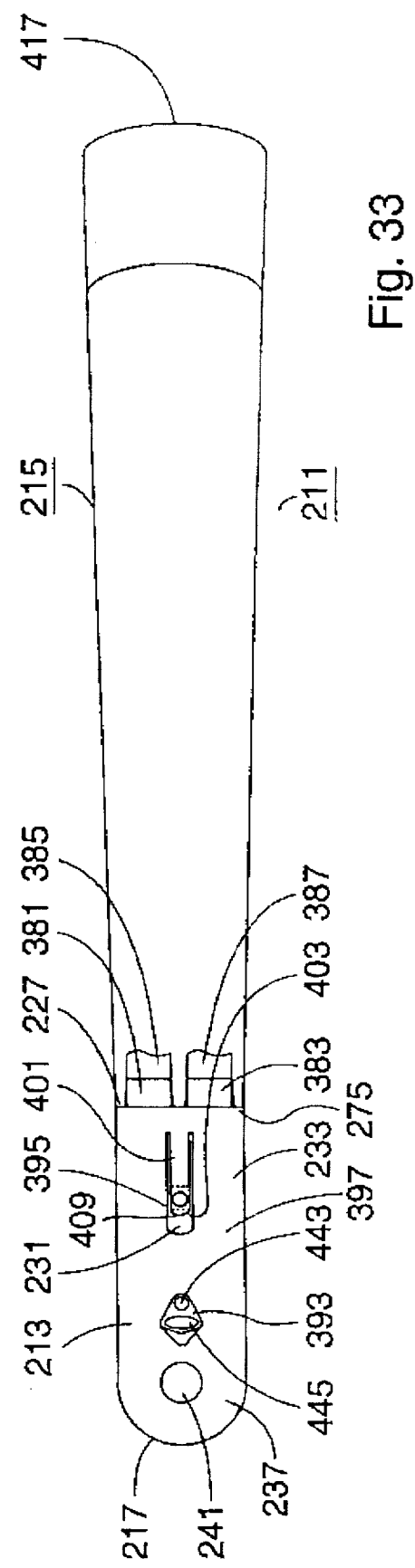

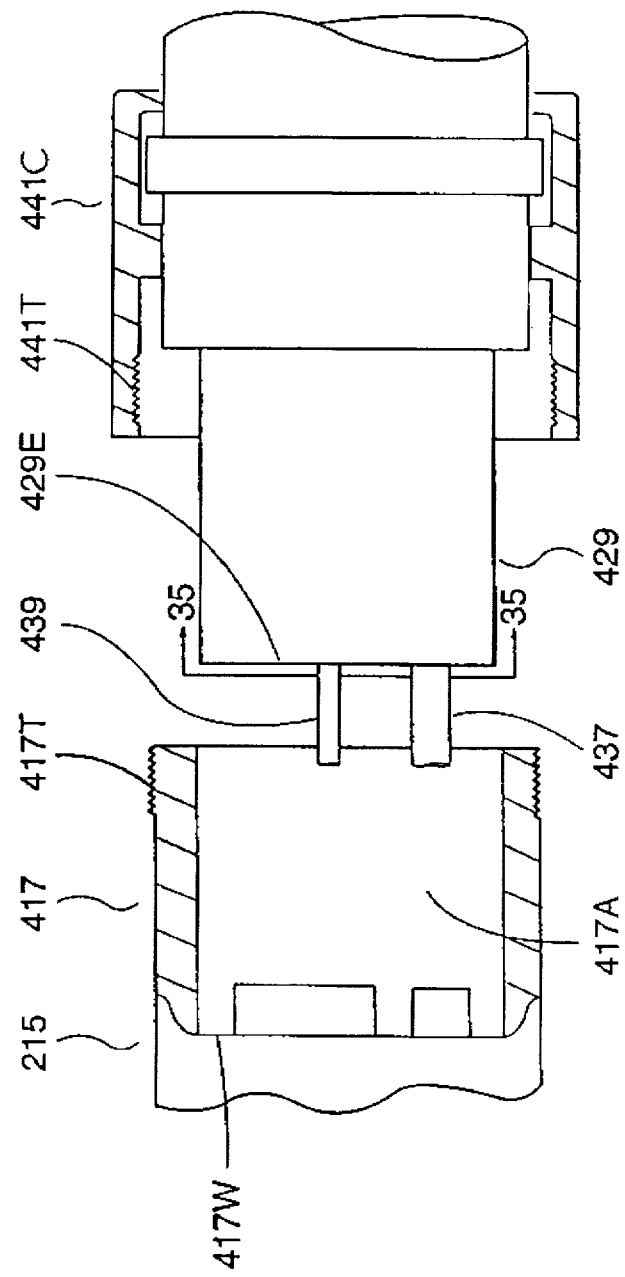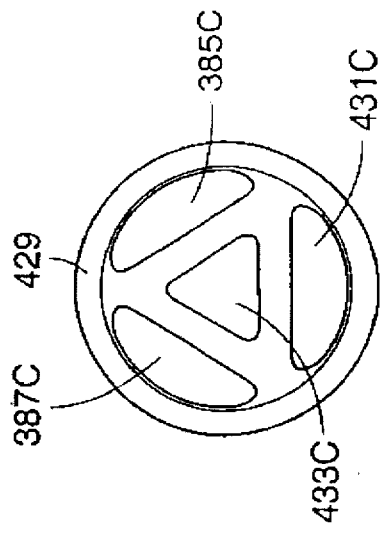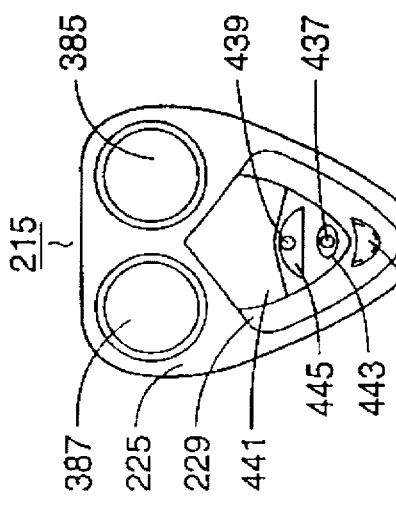

DENTAL HANDPIECE WITH DISPOSABLE DRILL HEAD ASSEMBLY

This is a continuation-in-part of U.S. Pat. Ser. No. 08/242,189, filed on May 13, 1994, now abandoned, which is a continuation-in-part of U.S. application Ser. No. 08/128,891, filed Sep. 30, 1993, now abandoned, which is a continuation-in-part of the prior application Ser. No. 07/928,815, Filed, Aug. 13, 1992, now abandoned.

BACKGROUND OF THE INVENTION

1. Field of the Invention

This invention relates to dental equipment, specifically, a reusable handpiece handle assembly interconnected with a disposable drill head assembly.

2. Description of the Related Art

Conventional high speed dental handpieces are one piece assemblies having an integrally coupled hand portion and head assembly. A rotary turbine is located in the head assembly. The turbine is driven at high speeds of approximately 150,000 to 300,000 rpm by compressed air applied to the turbine. The rotary action of the turbine turns a burr attached to the axle of the turbine. The burr is used for dental drilling. Air and water are delivered to the head assembly of the handpiece through tubing in the handle connected to a conventional dental stand which provides compressed air and water to the handpiece.

Conventional high speed dental handpieces are difficult to clean. In the process of drilling, organic matter and bacterial residue enter the head assembly of the handpiece and become attached to the intricate interior parts of the handpiece. The build up of foreign matter on the interior parts of the head assembly of the handpiece presents two problems: first, the organic matter and bacterial residue, and any diseases therein, may be transmitted to other dental patients by the force of the compressed air applied to the turbine; second, the build-up of foreign matter on the intricate parts of the handpiece eventually reduces the speed at which the handpiece operates to an extent that the handpiece becomes non-functional and must be replaced. Cleaning the intricate interior parts of the handpiece is not possible through normal disinfecting and sanitizing procedures such as rinsing or flushing. Autoclaving has been used to clean dental handpieces, however, autoclaving has proven :extremely time consuming and causes severe deterioration of the handpiece, thereby lessening the usable life-span of the device.

Dental handpieces with disposable drill heads have been introduced to address the cleaning problems inherent in conventional dental handpieces. Balson (U.S. Pat. No. 3,955,284) discloses a disposable dental drill assembly which has a drill head assembly that may be disposed after each use of the handpiece while the handle of the handpiece may be retained.

However, due to the arrangement of the turbine in the drill head assembly of the Balson device, the device has difficulty maintaining adequate drill speeds when pressure is applied to the burr of the device. The turbine, or rotor member, rotates about stub shafts that extend axially from the turbine blades. The stub shafts are located in seats in the drill head housing. When pressure is applied to the burr the pressure is transmitted directly to the stub shafts, forcing the shafts frictionally against the seats, thereby significantly reducing the speed of the burr.

Furthermore, Balson does not disclose means to accurately introduce air or water at the drilling area. Conventional dental handpieces have air and water passages that terminate adjacent the burr so that air and water may be accurately directed to the actual working surface of the dental drill. Balson does not provide air and water passages in the disposable drill head assembly. A water passage is provided in the neck of the device, a distance away from the actual working surface of the drill. The distance between the actual working surface of the drill and the water passage reduces the accuracy of delivery of water to the working surface.

Balson also does not provide protection against foreign matter entering the handle. A passage extends from a compressed air source through the handle of the device into the disposable drill head assembly. Compressed air is delivered to the turbine through the passage. Foreign matter that has accumulated in the drill head assembly may be sucked back into the passage in the handle upon cessation of application of compressed air to the turbine. The foreign matter may subsequently be transmitted to other dental patients by reapplication of compressed air through the passage even though a new drill head has been attached to the device.

SUMMARY OF THE INVENTION

It is, therefore, an object of this invention to provide a high speed dental handpiece having a disposable drill head assembly and a reusable handle, wherein the speed of a burr retained by the drill head assembly is unaffected by pressure placed on the burr;

It is a further object of the invention to provide a high speed dental handpiece having a disposable drill head assembly and a reusable handle capable of accurately delivering water, air and light to the actual working surface of the drill;

It is a still further object of the invention to provide a high speed dental handpiece having a disposable drill head assembly and a reusable handle having means to protect the handle from the introduction of foreign matter into the handle.

These and other objects of the invention are accomplished by providing a high speed dental apparatus having a reusable handle and a disposable head assembly.

The disposable head assembly comprises a housing having a head cavity with first and second openings at said first and second ends respectively leading to the head cavity. Also provided is a shaft having first and second ends, a turbine coupled to the shaft between the first and second ends of said shaft, a drill burr is adapted to be coupled to the second end of the shaft. The shaft, turbine are located in the head cavity with the drill burr extending out of the head cavity, when in place, by way of said second opening at said second end. First and second bearing means are located in said cavity for supporting said bearing, said turbine, and said drill burr for rotation. An air inlet channel and an air exhaust channel extend from the coupling end of said neck lead to the head cavity for directing air onto the turbine and from head cavity for rotating the turbine and the drill burr. A neck cavity extends from the coupling end of the neck to an outlet opening located close to and directed toward the drill burr extending out of the second end of the head.

In the preferred embodiment, the side wall of the housing is formed to engage and secure the first bearing means and hence the drill assembly in the head cavity of the housing.

A handle is provided which is adapted to be releasably coupled to the neck of the head assembly. The handle has a proboscis or nozzle end, adapted to be located in the neck cavity by way of the coupling end of the neck and to be located next to the outlet opening of the neck cavity when the handle is coupled to the head assembly. The handle has an air inlet channel and an air exhaust channel extending from an inlet end of said handle to an outlet end portion adapted to be coupled to the air inlet channel and the air exhaust channel respectively of the neck at the coupling end of the neck when the handle is coupled to the neck of the head assembly. The handle has at least two conduits extending from the inlet end of the handle to the proboscis or nozzle end for directing at least a fluid through the outlet opening of the neck cavity when the handle is coupled to the neck.

In a further aspect, a U-shaped opening is formed through the wall of the neck between the outlet opening of the cavity of said neck and the coupling end of the neck forming a resilient flap having a free end located closer to the outlet opening of the cavity of the neck than the coupling end of the neck. The handle has a protuberance extending therefrom near the proboscis end such that when the proboscis is inserted into the cavity of the neck, the protuberance is able to push the flap outward to allow the protuberance to be located between the free end of the flap and the outlet opening of the cavity of the neck to secure the handle to the neck of the head. The flap may be broken away to allow the handle to be removed from the head assembly to allow disposal of the head assembly.

A one-way valve is provided in the air inlet channel of the handle to allow flow therethrough only from the inlet end of the handle.

BRIEF DESCRIPTION OF THE DRAWINGS

FIG. 4 is a side perspective view of another embodiment of the invention having a notched coupling mechanism.

FIG. 5 is an exploded view of a disposable head assembly, neck portion of the handle, and the body of a handle where the disposable head assembly and the nozzle of the neck portion are shown in cross-section.

FIG. 19 is a bottom view of the head assembly of FIG. 13.

FIG. 21 is an end view of the handle as seen from lines 21—21 of FIG. 20.

FIG. 22 is a cross-sectional view of the handle as seen from lines 22—22 in FIG. 20.

FIG. 23 is a cross-sectional view of the handle as seen from lines 23—23 in FIG. 20.

FIG. 24 is a cross-sectional view of the handle as seen from lines 24—24 in FIG. 20.

FIG. 25 is a cross-sectional view of the handle as seen from lines 25—25 in FIG. 20.

FIG. 26 is a cross-sectional view of the handle as seen from lines 26—26 in FIG. 20.

FIG. 27 is an end view of the handle of FIG. 20 as seen from lines 27—27 of FIG. 20.

FIG. 28 is a top view of the handle of FIG. 20.

FIG. 29 is a bottom view of the handle of FIG. 20.

FIG. 32 is a partial cross-sectional side view of the head of FIG. 13 coupled to the handle of FIG. 20.

FIG. 33 is a bottom view of the head of FIG. 13 coupled to the handle of FIG. 20.

FIG. 34 is a side cross-sectional view of the inlet end of the handle of FIG. 20 and a connector from a dental stand.

FIG. 35 is an end view of the handle as seen from lines 35—35 in FIG. 34.

FIG. 36 is an enlarged end view of the handle of FIG. 20 showing the light pipe and water pipe therein.

DESCRIPTION OF THE PREFERRED EMBODIMENTS

Figure 1:
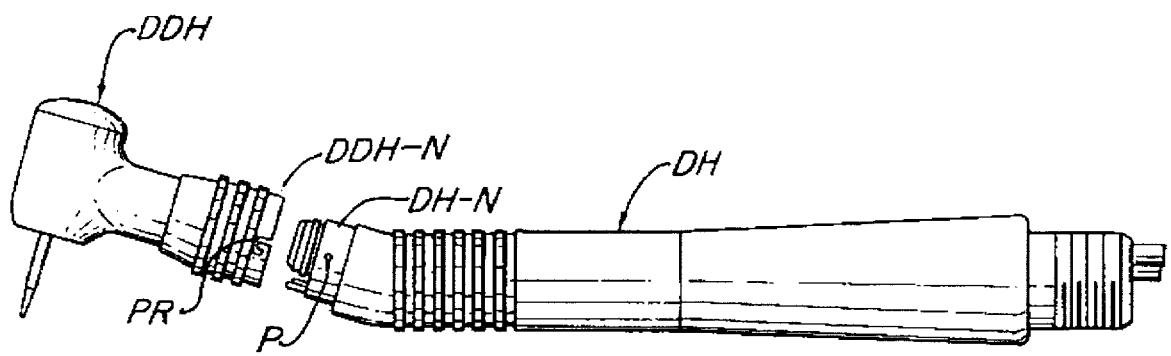
FIG. 1 is a perspective side view of one embodiment of the invention having a locking collar coupling mechanism.

Referring now to FIGS. 4 and 5, there is illustrated the high speed dental handpiece 11 of one embodiment of the invention. The handpiece 11 includes a handle 13 and a disposable head assembly 15 that is removably coupled to the handle 13. The disposable head assembly 15 retains a dental drill assembly 17.

The handle 13 of the handpiece 11 includes a generally cylindrical body portion 19 and a neck portion 21 extending at an angle from the body portion 19 at a neck end 23A of the body portion 19. A wide air conduit 25, a narrow air conduit 27, and a water conduit 29 extend from the end of the body portion 23B opposite the neck end 23A. The air conduits 25, 27 and water conduit 29 are connected to a generally conventional dental stand (not shown) which includes a compressed air source and a water source.

The cylindrical body portion 19 of the handle 13 is generally hollow. A turbine air intake tube 31 and a drying air intake tube 33 extend through the body 19 of the handle and communicate with the compressed air source by coupling the conduits 25, 29, respectively. A water tube 35 also extends through the body 19 of the handle 13 and communicates with the water source by coupling the water conduit 27.

An exhaust tube 32 extends through the handle to an exhaust conduit 26. The exhaust tube 32 accepts exhaust from the head assembly 15 and delivers it to the exhaust conduit 26. The exhaust conduit 26 is connected to a sewer line (not shown) for disposal of the exhaust.

A fiber optics connector 37 also extends from the end of the body 23B opposite the neck end 23A. The fiber optics connector 37 is connected to a fiber optics light source (not shown), which may be included in the conventional dental stand. A fiber optics tube 39 extends through the handle 13 and communicates with the fiber optics connector 37 at the end 23B of the handle 13. The fiber optics tube 39 extends through the handle 13 to the neck 19 of the handle 13. Fiber optics extend through the handle 13 in the fiber optics tube 39.

The handle 13 of the dental handpiece 11 and the disposable head assembly 15 are coupled about the neck portion 21 of the handle 13. In a preferred embodiment, as shown in FIG. 5, the neck 19 has a cylindrical threaded coupling section 41, an angled joining section 43, and a projecting nozzle 45. The threaded coupling section 41 extends into, is received by, and is removably coupled to a threaded bore in the neck end 23A of the body 19 of the handle 13, which has an inner diameter slightly larger than the outer diameter of the coupling section 41.

Figure 12:
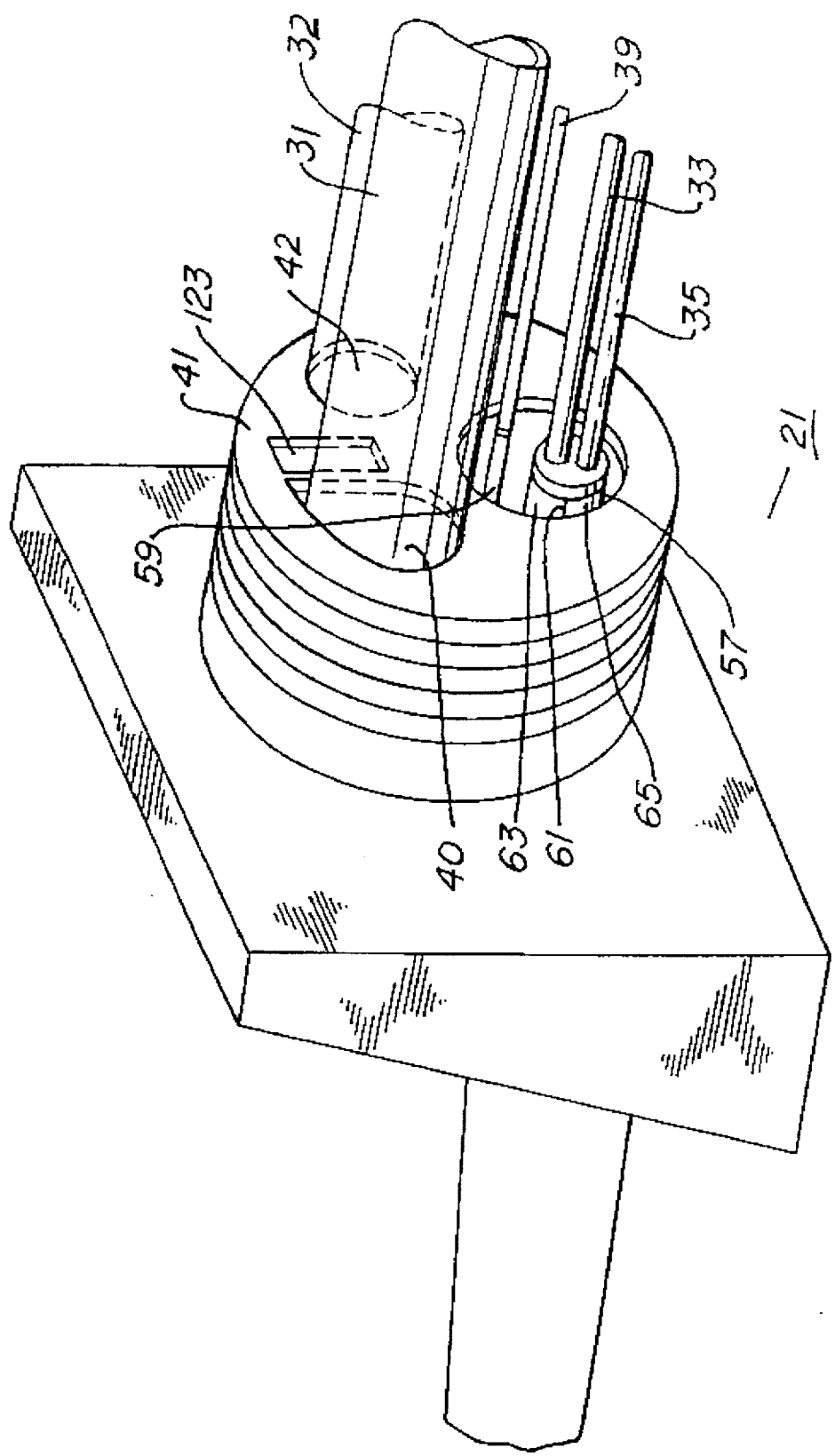
FIG. 12 is a perspective view of the neck portion of the handle.

As shown in FIG. 12, the tubes 31, 32, 33, 35 and 39 are coupled to passages or tubes extending through the neck 21 of the handle 13. The turbine air intake tube 31 is coupled to a turbine air intake passage 40. The exhaust tube 32 is coupled to an exhaust passage 42. The fiber optics tube 39 is coupled to a fiber optics illuminating tube 59. The drying air tube 33 is coupled to an air delivery section 63 of an air/water delivery tube 57, and the water tube 35 is coupled to a water delivery section 65 of the air/water delivery tube 57. Preferably, the tubes 31, 32, 33, 35, and 39 are coupled to the passages 40, 42 and tubes 57, 59 by being soldered therein when the neck 21 is apart from the body 19 of the handle 13. To attach the neck 21 to the body 19 of the handle 13 the tubes 31, 32, 33, 35 and 39 are located within the bore in the neck end 23A of the body 19. The tubes 31, 32, 33, 35 and 39 are extended through the body 19 by bringing the neck 21 together with the body 19 of the handle 13. When the neck 21 has been coupled to the body 19 about the threaded coupling section 41 the tubes 31, 32, 33, 35 and 39 have sufficient length to extend through the body 19 to the end 23B of the body 19 so that the conduits 25, 26, 27, 29 and the fiber optics connector 37 may be coupled to the tubes 31, 32, 35, 33 and 39.

Referring now to FIG. 5, the threaded coupling section 41 of the neck 21 is integrally coupled to and extends from the angled joining section 43. The angled joining section 43 is located abutting the neck end 23A of the body 19 when the coupling section 41 is located in the threaded bore. The angled joining section 43 forms an angled joint between the body 19 of the handle 13 and the head assembly 15 when the head assembly 15 is coupled to the handle 13.

The projecting nozzle 45 of the neck 29 is integrally coupled to the angled joining section 43 and extends away from the neck end 23A of the body 19 of the handle 13. The nozzle 45 is generally conical in shape, having a base 47 located abutting the angled joining section 43, and having a tip 49. The nozzle 45 is generally hollow, having a nozzle wall 51 located about and encompassing a nozzle cavity 53. A nozzle opening 55 is located near the tip 49 of the nozzle 45 along the bottom of the nozzle 45. The nozzle opening 55 communicates with the cavity 53 enclosed by the nozzle wall 51.

The air/water delivery tube 57, and the fiber optics illuminating tube 59 extend parallel to each other through the cavity 53 of the nozzle 45 from the base 47 of the nozzle 45 to a location adjacent to the nozzle opening 55. The air/water delivery tube 57 is capable of spraying water from the water source and blowing air from the compressed air source through the nozzle opening 55. The air/water delivery tube 57 is coupled to the drying air intake tube 33 and the water tube 35 through the neck end 23A of the body 19. The air/water delivery tube 57 has a dividing wall 61 extending across the diameter of the tube 57 which separates the tube 57 into an air delivery section 63 and a water delivery section 65. The water tube 35 is coupled to the water delivery section 65, and the drying air intake 33 is coupled to the air delivery section 63. The dividing wall 61 terminates near the nozzle opening 55 so that air and water from the air delivery section 63 and the water delivery section 65 can be combined in order to spray a mist through the nozzle opening 55.

The fiber optics illuminating tube 59 carries fiber optics to the nozzle opening 55, where the fiber optics may emit light through the nozzle opening 55. The fiber optics illuminating tube 59 is coupled to the fiber optics tube 39 through the neck end 23A of the body 19 (see FIG. 12). Fiber optics extend from the fiber optics light source through the fiber optics connector 37, through the fiber optics tube 39, and through the fiber optics illuminating tube 59 in the nozzle 45 to the nozzle opening 55.

As shown in FIGS. 5 and 12, the turbine air intake passage 40 and the exhaust passage 42 extend through the neck portion 21 of the handle 13. The turbine air intake passage 40 and the exhaust passage 42 extend through the angled joining section 43 above and to the sides, respectively, of the nozzle 45. In a preferred embodiment, a flap valve 66 is located across the turbine air intake passage 40 in the neck 19 of the handle 13 to prevent foreign material from being sucked back into the handle 13. The flap valve 66 may be any conventional valve that can be opened by positive air pressure on one side of the valve, but closes, or remains closed in the absence of positive air pressure on that side of the valve.

Referring now to FIGS. 5–11 of the drawings, a preferred embodiment of the disposable head assembly 15 is illustrated. The head assembly 15 has a drill head portion 67, a cylindrical connecting portion 69, and a connecting prong 71. The drill head portion 67 contains the drill assembly 17 therein. The cylindrical connecting portion 69 integrally couples the drill head portion 67 and extends between the drill head portion 67 and the handle 13 of the handpiece 11. The connecting prong 71 is integrally coupled to the cylindrical connecting portion 69 and extends outwards from the connecting portion 69 away from the drill head portion 67. The connecting prong 71 removably couples the head assembly 15 to the handle 13 of the handpiece 11.

The drill head portion 67 and the connecting portion 69 form a housing 73 for the dental drill assembly 17. The drill head portion 67 has a housing cavity 75 located therein. The housing cavity 75 is connected to an air intake passage 77 and a head exhaust passage 79. The air intake passage 77 extends from an air intake passage outlet 77(O) in the housing cavity 75 through the connecting portion 69 to a neck end of the connecting portion 69N. The air intake passage 77 in the disposable head assembly 15 and the turbine air intake passage 40 in the neck 21 of the handle 13 are continuously connected when the handle 13 and the head assembly 15 are coupled so that compressed air from the compressed air source may be delivered to the housing cavity 75. The head exhaust passage 79 extends from a head exhaust passage outlet 79(O) in the housing cavity 75 to the neck end of the connecting portion 69N. The head exhaust passage 79 in the disposable head assembly 15 and the exhaust passage 42 in the neck of the handle 13 are continuously connected when the handle 13 and head assembly 15 are coupled so that exhaust air from the housing cavity 75 may be removed through the handle 13.

Figure 6:
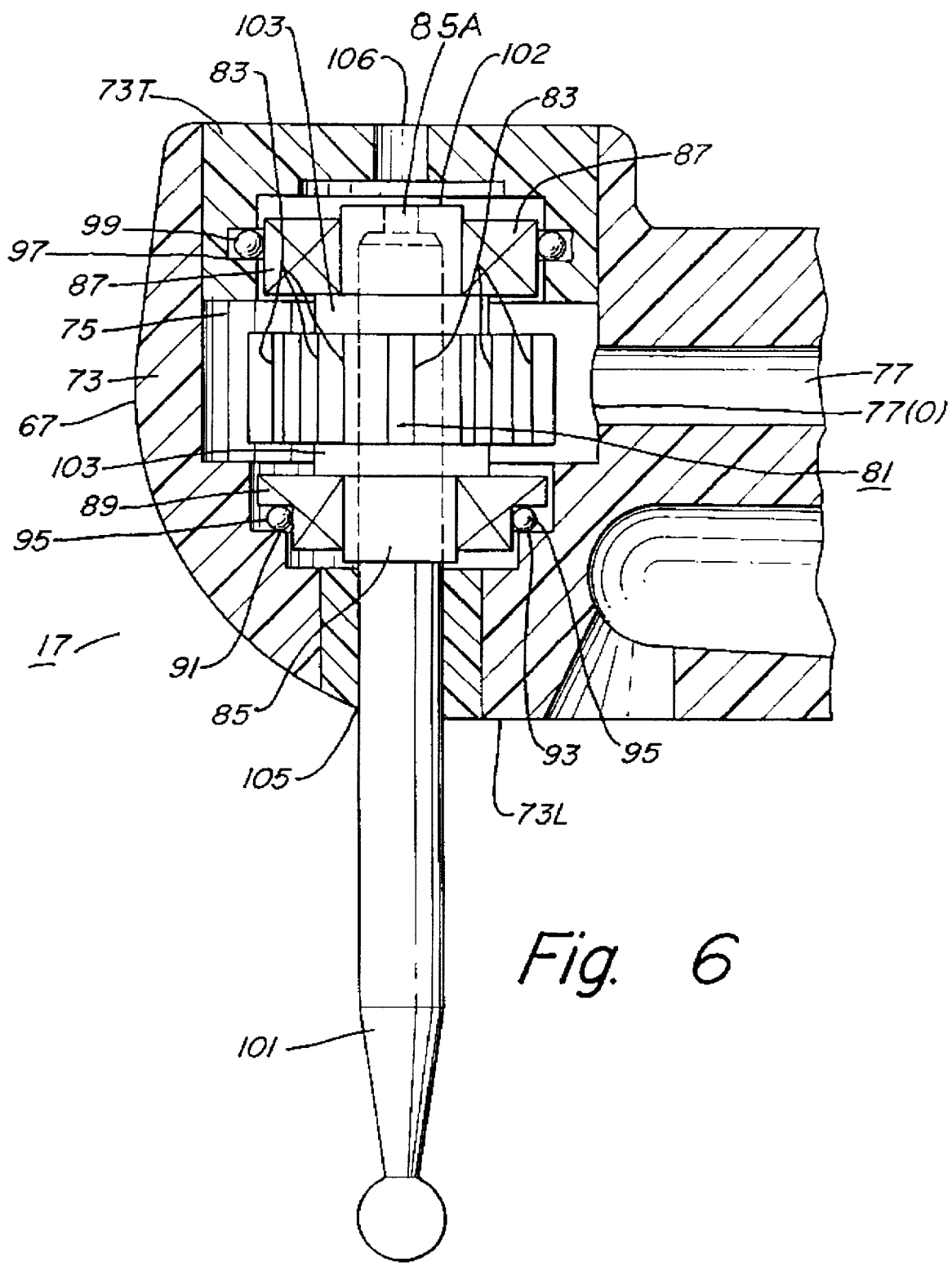
FIG. 6 is a cross-sectional view of a disposable head assembly of the invention having a notched coupling mechanism.
Figure 9:
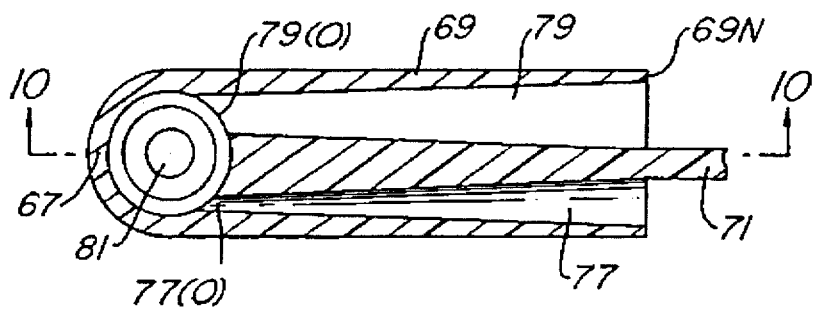
FIG. 9 is a cross-sectional view of the disposable head assembly as seen from lines 9—9 of FIG. 7.
Figure 10:
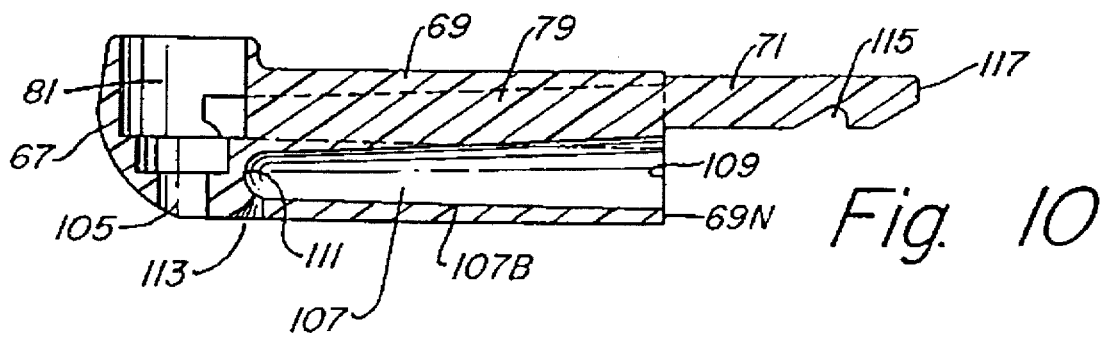
FIG. 10 is a cross-sectional view of the disposable head assembly as seen from lines 10—10 of FIG. 9.
Figure 11:
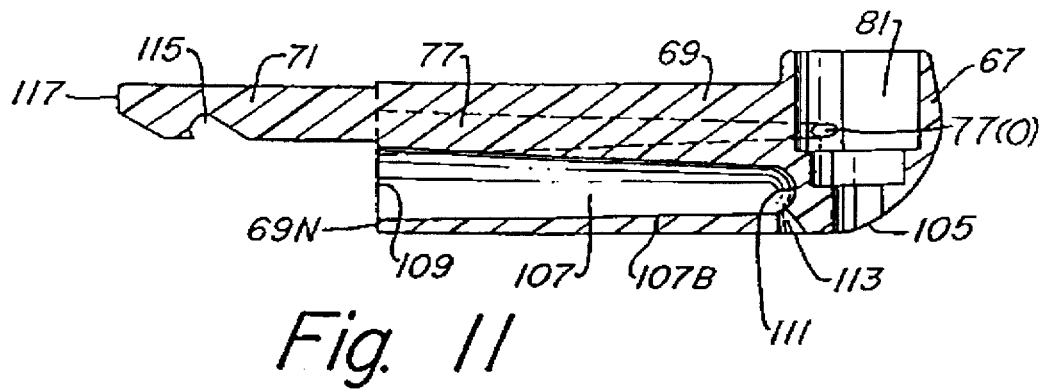
FIG. 11 is a cross-sectional view of the disposable head assembly as seen from lines 11—11 of FIG. 7.

As shown in FIG. 6, the dental drill assembly 17 is located in, and has a burr 101 extending through, the housing cavity 75 located in the drill head portion 67 of the disposable head assembly 15. A rotary member 81 is rotatably located in the cavity 75. The rotary member 81 has a plurality of turbine blades 83 which may be driven by air flow from the compressed air source. The air intake passage 77 terminates adjacent the turbine blades 83 so that compressed air moving through the air intake passage 77 will drive the turbine blades 83 upon exiting the air intake passage 77. The outlet of the air intake passage 77(O) is narrower than the remainder of the intake passage 77 so that the pressure of the compressed air is increased as the air reaches the turbine blades 83. As can be seen in FIG. 9, the head exhaust passage 79 also terminates adjacent the turbine blades 83 so that exhaust air from the turbine blades 83 may be rapidly removed from the housing cavity 75.

Referring back to FIG. 6, the rotary member 81 is rotatably seated in the housing 73 of the drill head portion 67. The turbine blades 83 are coupled to and rotate with a shaft 85 which extends through the axis of the rotary member 81. The shaft 85 is oriented in the housing cavity 75 so that the shaft 75 extends vertically in the head assembly 15. Upper and lower bushings 87, 89 are coupled to the shaft 85 above and below the turbine blades 83. The rotary member 81 is rotatably seated on the upper and lower bushings 87, 89. The lower bushing 89 and a lip 91 formed by the housing 73 form a lower race 93 in which lower bearings 95 are located. The lower bushing 89 is rotatably located in the housing 73 on the lower bearings 95. The upper bushing 87 and the housing 73 form an upper race 97 in which upper bearings 99 are located. The upper bushing 87 is rotatably located in the housing 73 against the upper bearings 99.

A burr 101 for drilling is removably coupled to the rotary member 81. The burr 101 is removably attached to the rotary member 81 by generally conventional friction fit rings 103 located in the shaft 85. The burr 101 is caused to rotate for drilling when the turbine blades 83 are driven by air flow from the compressed air source thereby rotating the shaft 85 which in turn rotates the burr 101. The friction fit rings 103 hold the burr 101 in a fixed vertical location. The burr 101 extends out of the cavity 75 through a burr aperture 105 located in the lower face of the housing 73L. The burr 101 is inserted into the shafts 85 through the burr aperture 105. The burr 101 is inserted upwards through the friction fit rings 103 in the shaft 85 until the burr 101 reaches the upper wall 102 of the shaft 85. The upper wall 102 of the shaft 85 impedes any further upward movement of the burr 101 in the shaft 85.

A burr removal aperture 106 is located in the top of the housing 73T through which a burr removal instrument may be inserted for dislodging the burr 101 from the friction fit rings 103. The burr 101 may be dislodged from the shafts 85 by inserting the burr removal instrument through opening 85A and forcing the burr 101 downwards out of the friction fit rings 103. Various burrs 101 may be inserted in the rotary member 81.

Figure 7:
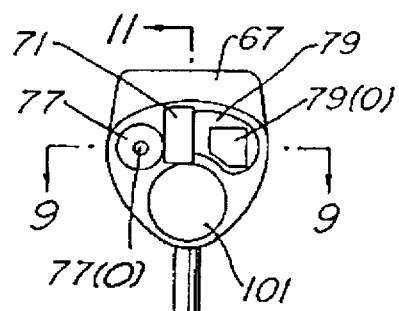
FIG. 7 is an end view of a disposable head assembly of the invention having a notched coupling head viewing from the neck end of the head assembly towards the drill head portion.
Figure 8:
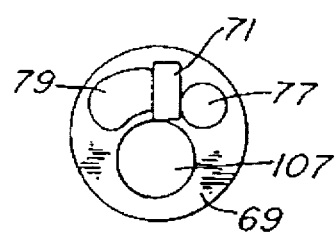
FIG. 8 is a view of the connecting portion of a disposable head assembly of the invention looking rearward away from the drill head portion.

Referring now to FIGS. 5 & 7–11, the cylindrical connecting portion 69 of the disposable head assembly 15 integrally couples the drill head portion 67 and extends between the drill head portion 67 and the handle 13. As described above, the air intake passage 77 and the head exhaust passage 79 extend through the connecting portion 69 between the neck 21 of the handle 13 and the housing cavity 75 of the drill head portion 67. A nozzle receptacle 107 also extends through the connecting portion 69. The nozzle receptacle 107 is adapted to matingly receive the nozzle 45 of the neck portion 21 of the handle 13 therein. The nozzle receptacle 107 is centrally located in the lower half of the connecting portion 69, having a base 109 located adjacent to the neck end of the connecting portion 69N and a tip 111 located adjacent the burr aperture 105 in the lower face of the housing 73L. As shown in FIGS. 7, 8, the air intake passage 77 and the head exhaust passage 79 extend through the connecting portion 69 above and to each side, respectively, of the nozzle receptacle 107.

The nozzle receptacle 107 is located to allow the air/water delivery tube 57 and the fiber optics illuminating tube 59 in the nozzle 45 to deliver air, water and light to the operating surface of the handpiece 11. An emission aperture 113 is located at the tip 111 along the bottom of the nozzle receptacle 107B and is directed from the nozzle receptacle 107 through the lower face of the housing 73L towards the burr 101. The emission aperture 113 and the nozzle opening 55 of the nozzle 45 align when the nozzle 45 is located in the nozzle receptacle 107. The air/water delivery tube 57 is positioned to deliver air and water through the nozzle opening 55 and the emission aperture 113 to the burr 101 and the operating surface of the handpiece 11. The fiber optics tube 59 is positioned to deliver light through the nozzle opening 55 and the emission aperture 113 to the same location.

The connecting prong 71 removably couples the disposable head assembly 15 to the handle 13. As shown in FIGS. 5, 7, the connecting prong 71 is integrally coupled to the connecting portion 69 of the head assembly 15 above the nozzle receptacle 107 between the air intake passage 77 and the head exhaust passage 79, extending away from the connecting portion 69 and the drill head portion 67 of the head assembly 15. The connecting prong 71 has the shape of a key blade having a single notch 115, where the base of the blade is coupled to the connecting portion 69 of the head assembly 15 and the notched end 117 of the prong 71 is located away from connecting portion 69.

As shown in FIGS. 4, 5 and 12, the handle 13 accepts the connecting prong 71 therein through a notch receptacle 123 the neck 21 of the handle 13 and through the threaded bore of the body 19 of the handle 13. The notch 115 of the connecting prong 71 aligns with a pin aperture 119 in the handle 13 when the head assembly 15 is coupled with the handle 13. A retractable connecting pin 121 may be inserted through the pin aperture 119 and through the notch 115 to firmly couple the head assembly 15 and the handle 13 together.

In a preferred embodiment, the head assembly 15 is formed of a suitable plastic material by conventional molding techniques. Preferably the head assembly 15 is formed by an injection molding process. The head assembly 15 is formed in two parts 15A, 15B. The rotary member 81 is seated in the bottom part 15B of the assembly 15 and the top part of the assembly 15A is joined to the bottom part 15B enclosing the rotary member 81 therein. The handle 13 is formed of a durable stainless steel.

Figure 2:
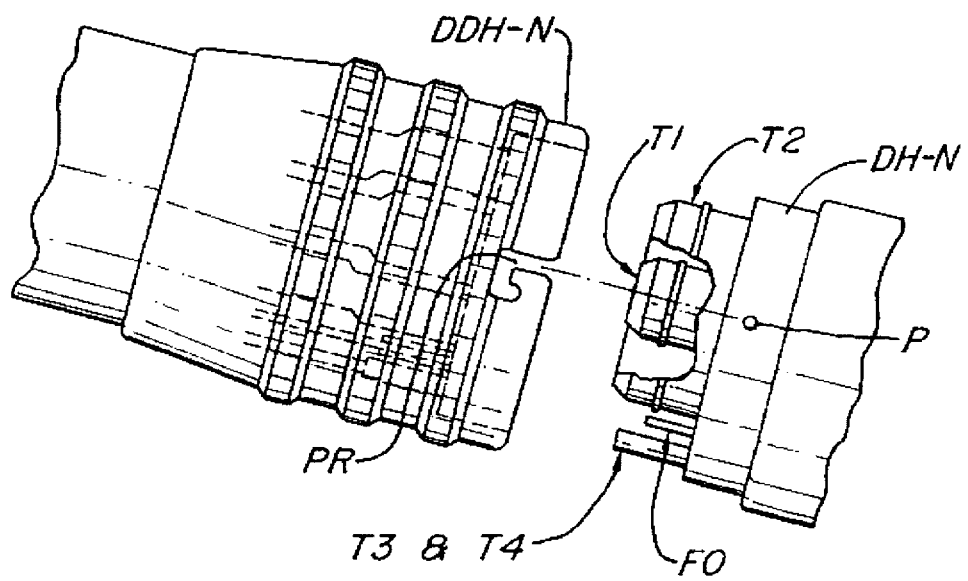
FIG. 2 is a enlarged view of the coupling or locking collar.
Figure 3:
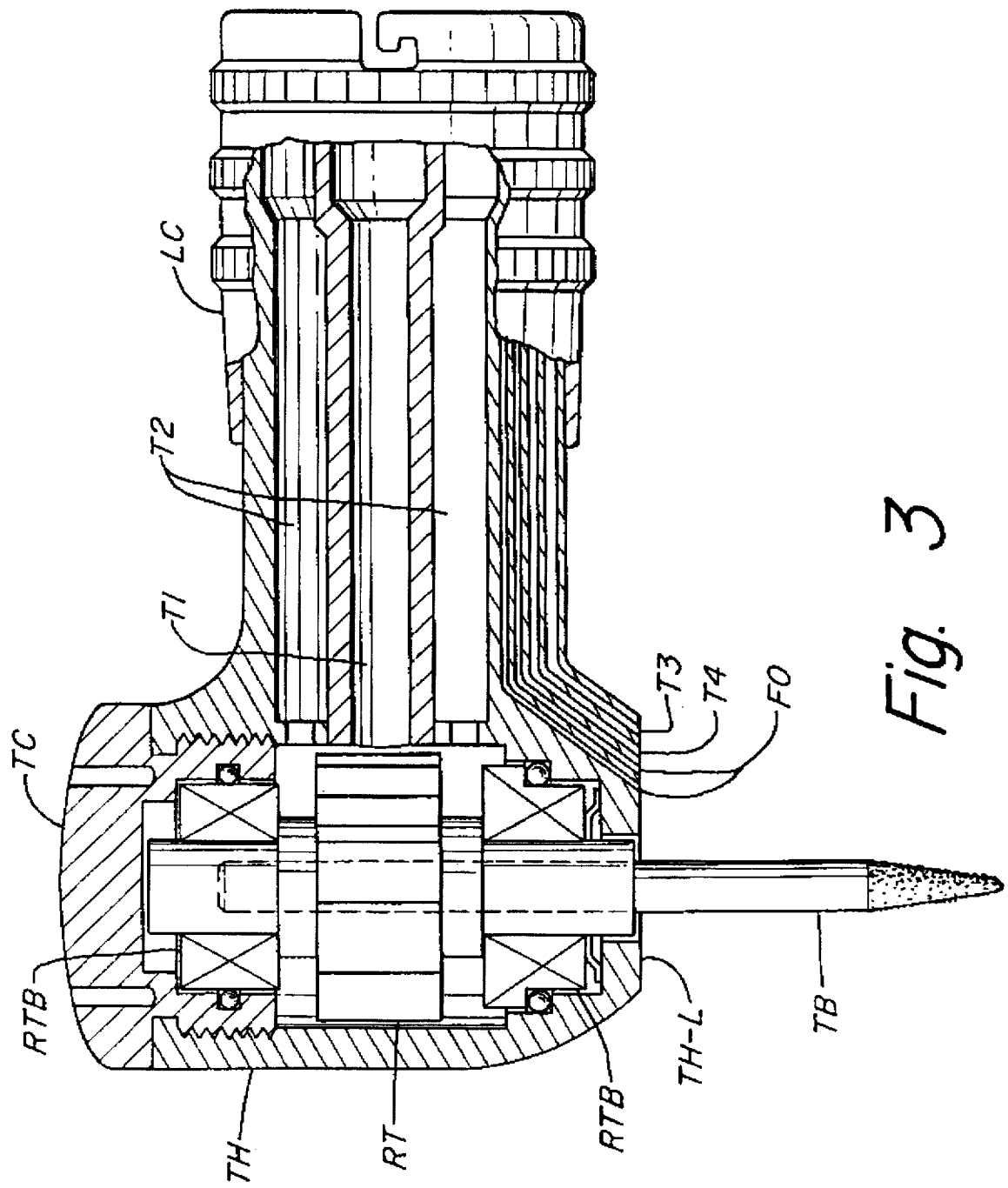
FIG. 3 is a cross-sectional view of a disposable dental head having a locking collar mechanism.

Referring now to FIGS. 1–3, another embodiment of the invention is shown. Both the dental handpiece DH and the disposable dental head DDH are generally similar to the handle 13 and the disposable head assembly 15, respectively, of the embodiment disclosed above. As shown in FIG. 3, the disposable dental head DDH has a tool bit TB rotated by a rotary turbine RT mounted on rotary turbine bearings and bushings RTB in a turbine housing TH capped by a turbine Chuck TC. Compressed air from a compressed air source such as a conventional dental stand is delivered through a motor air in connector tube T1 in the disposable dental head DDH to drive the rotary turbine RT. Turbine exhaust is removed from the turbine housing TH and the disposable dental head DDH through a motor air out connector tube T2. As shown in FIGS. 1 and 2, the motor air in connector tube T1 and the motor air out connector tube T2 extend through the dental handpiece DH. At the end of the dental handpiece DH opposite the disposable dental head DDH the motor air in connector tube T1 may be connected to a compressed air source, and the motor air out connector tube T2 may be coupled to a disposal line. Cooling air and water tubes T4, T3 and fiber optics FO also extend through the dental handpiece DH, being connected between a conventional air, water, and light source, respectively, and the disposable dental head DH.

Although the dental handpiece DH and the disposable dental head DDH are generally similar to the handle 13 and the disposable head assembly 15 previously disclosed, a different means for coupling the dental handpiece DH and the disposable dental head DDH is disclosed, and different means for delivering air, water and light to the operating surface of the drill are disclosed. As shown in FIGS. 1 and 2, the disposable dental head DDH is removably coupled to the dental handpiece DH with a locking collar coupling LC at a neck end of the dental handpiece DH-N. The disposable dental head DDH has a neck DDH-N that is formed with a counterbore which receives the neck end of the dental handpiece DH-N therein. The neck end of the dental handpiece DHoN is formed with a plurality of outward projections P, only one of which is shown. The neck of the disposable dental head DDH-N has a matching number of projection receptacles PR therein. Together the outward projections P and the projection receptacles PR form an easily removable interlocking connection between the dental handpiece DH and the disposable head assembly DDH.

As shown in FIGS. 2 and 3, water, air and light are conducted to the operating surface of the drill through the dental handpiece DH and the disposable dental head DDH. A cooling air connecting tube T4 conducts compressed air from a compressed air source through the length of the dental handpiece DH to the neck end of the dental handpiece DH-N. The cooling air connecting tube T4 connects between the dental handpiece DH and the disposable dental head DDH. The cooling air connecting tube T4 extends through the disposable dental head DDH to the lower face of the turbine housing TH-L of the dental head DDH. The cooling air connecting tube T4 terminates at an opening in the lower face of the turbine housing TH-L from which compressed air may be blown onto a surface drilled by the tool bit TB.

A cooling water connecting tube T3 conducts water from a water source through the length of the dental handpiece DH to the neck end of the dental handpiece DH-N. The cooling water connecting tube T3 connects between the dental handpiece DH and the disposable dental head DDH. The cooling water connecting tube T3 extends through the disposable dental head DDH to the lower face of the turbine housing TH-L of the dental head DDH. The cooling water connecting tube T3 terminates at an opening in the lower face of the turbine housing TH-L from which water may be sprayed onto a surface drilled by the tool bit TB.

Fiber optics FO conduct light from a light source through the length of the dental handpiece DH to the neck end of the dental handpiece DH-N. The fiber optics FO connect between the dental handpiece DH and the disposable dental head DDH. The fiber optics FO extend through the dental head DDH to the lower face of the turbine housing TH-L. The fiber optics FO terminate at an opening in the lower face of the turbine housing TH-L through which light may be shined on the surface drilled by the tool bit TB.

Referring to FIGS. 13–41 there will be described a high speed dental handpiece 211 of the present invention in accordance with the preferred embodiment. The handpiece 211 includes a disposable head assembly 213 and a reusable handle 215 which are removably coupled together. Like numbers in FIGS. 13–41 and FIGS. 4–12 designate similar parts and components.

The head assembly 213 comprises a housing 217 formed of plastic material forming a cavity 75 with a top end 235 and a bottom end 237 forming top and bottom openings 239 and 241 leading to the cavity 75 in which is located a turbine operated drill assembly 223 with a drill burr 101 extending out of the lower opening 241. The upper wall 235 of the housing is pressed, formed, or folded against the top of the drill assembly 213 with an ultrasonic tool and secured in place by ultrasonic welding to permanently fix the drill assembly 223 in the cavity 75 such that the bearing mechanism for rotatably supporting the turbine and drill burr is integral with the head assembly 213.

The head assembly 213 also has a neck 233 with a cavity 389 for removably receiving the proboscis 229 of the handle 215 by way of a rear opening 391. The handle 215 has a front end 225 which engages the rear end 227 of the head assembly when the two units are coupled together. The handle 215 supplies and removes air for operating the turbine and also supplies air, water and light from the proboscis 229 which are directed toward the burr 101 by way of an outlet opening 393. The handle 215 is snap-locked to the head assembly 213 when the proboscis is located in the neck cavity 389. A protuberance 231 extends from the proboscis 229 for snap-locking the handle 215 and the head assembly together. The lock mechanism of the head assembly is broken away to remove the head assembly from the handle after which the head can be discarded.

Figure 13:
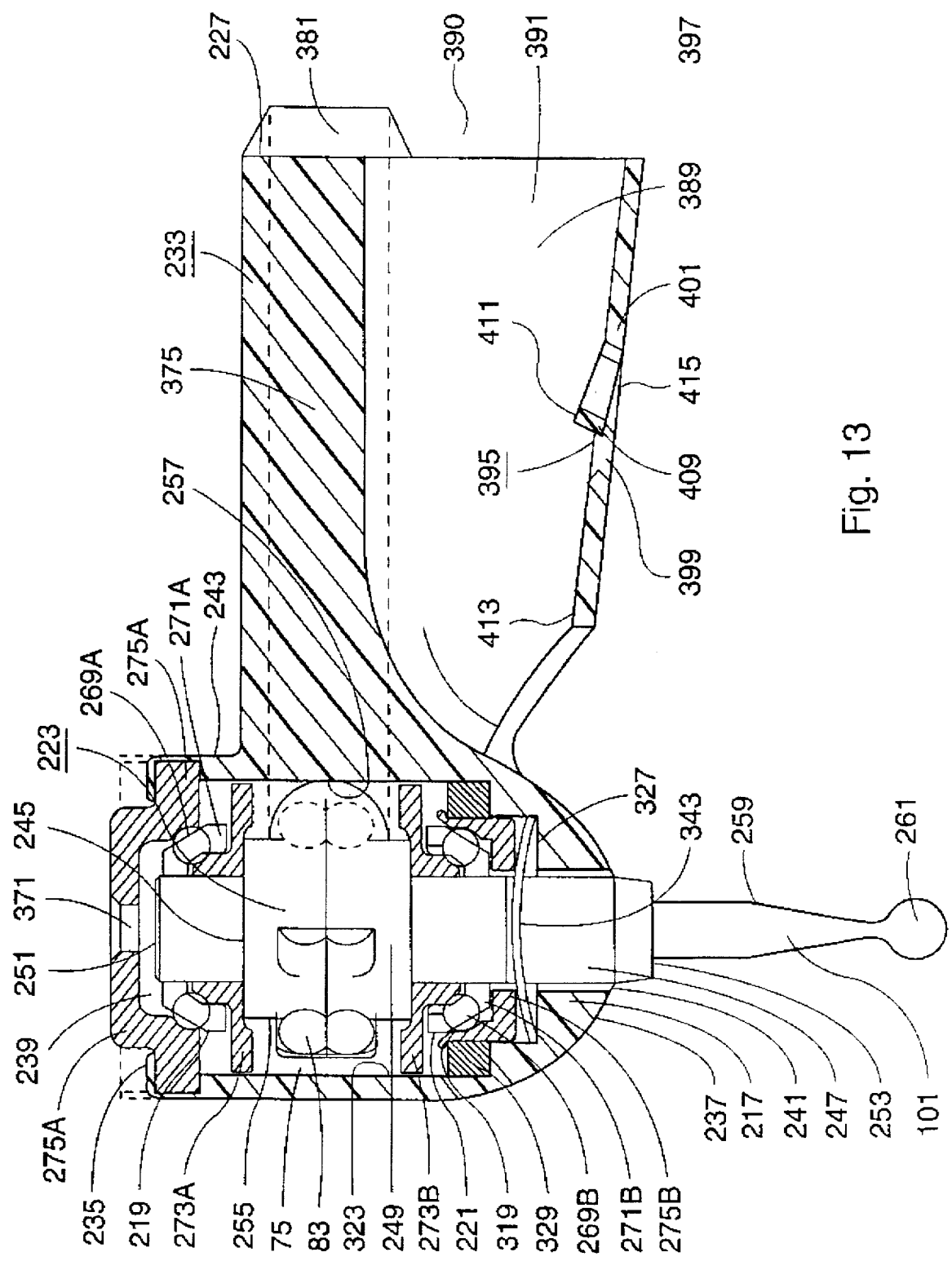
FIG. 13 is a side cross-sectional view of the head assembly of the preferred embodiment of the invention.
Figure 14:
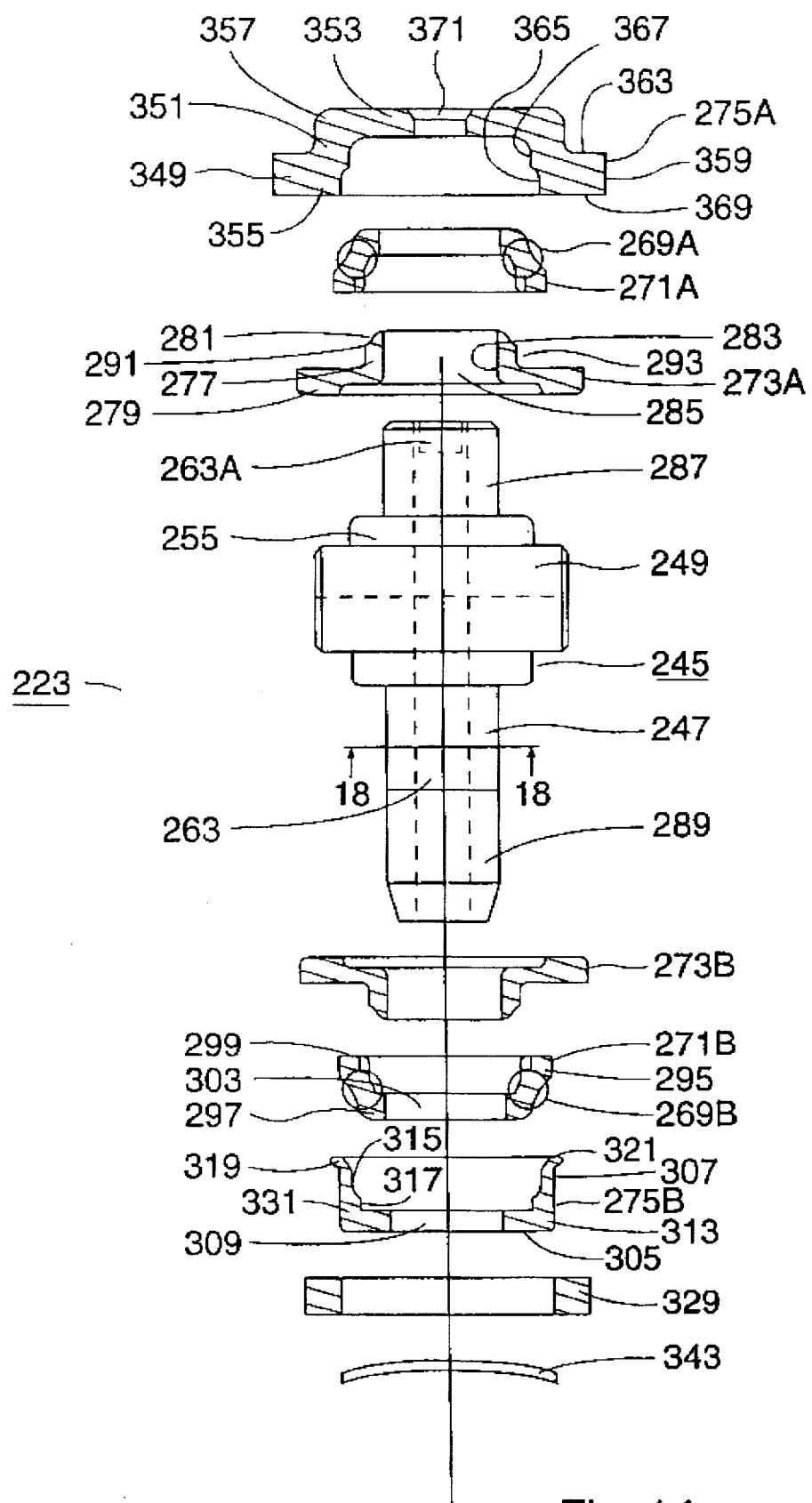
FIG. 14 is an exploded view of the drill assembly of the head of FIG. 13.

As shown in FIGS. 13 and 14, the drill assembly 223 includes a rotor 245 and a drill burr 101 coupled to rotate together, and upper and lower bearings 219 and 221 for supporting the rotor 245 in the cavity 75 of the housing 217 so the rotor 245 may rotate relative to the housing 217. The rotor 245 has a shaft portion 247 and a turbine portion 249. The shaft portion 247 is substantially cylindrical and is located in the cavity 75 with its longitudinal axis oriented to extend from the top of the cavity 75 through the bottom opening 241 in the bottom end 237 of the housing. The top end 251 of the shaft portion 247 is located adjacent the top of the cavity within the housing 217 and the bottom end 253 of the shaft portion 247 is located proximate to the bottom opening 241 outside the housing 217.

Figure 15:
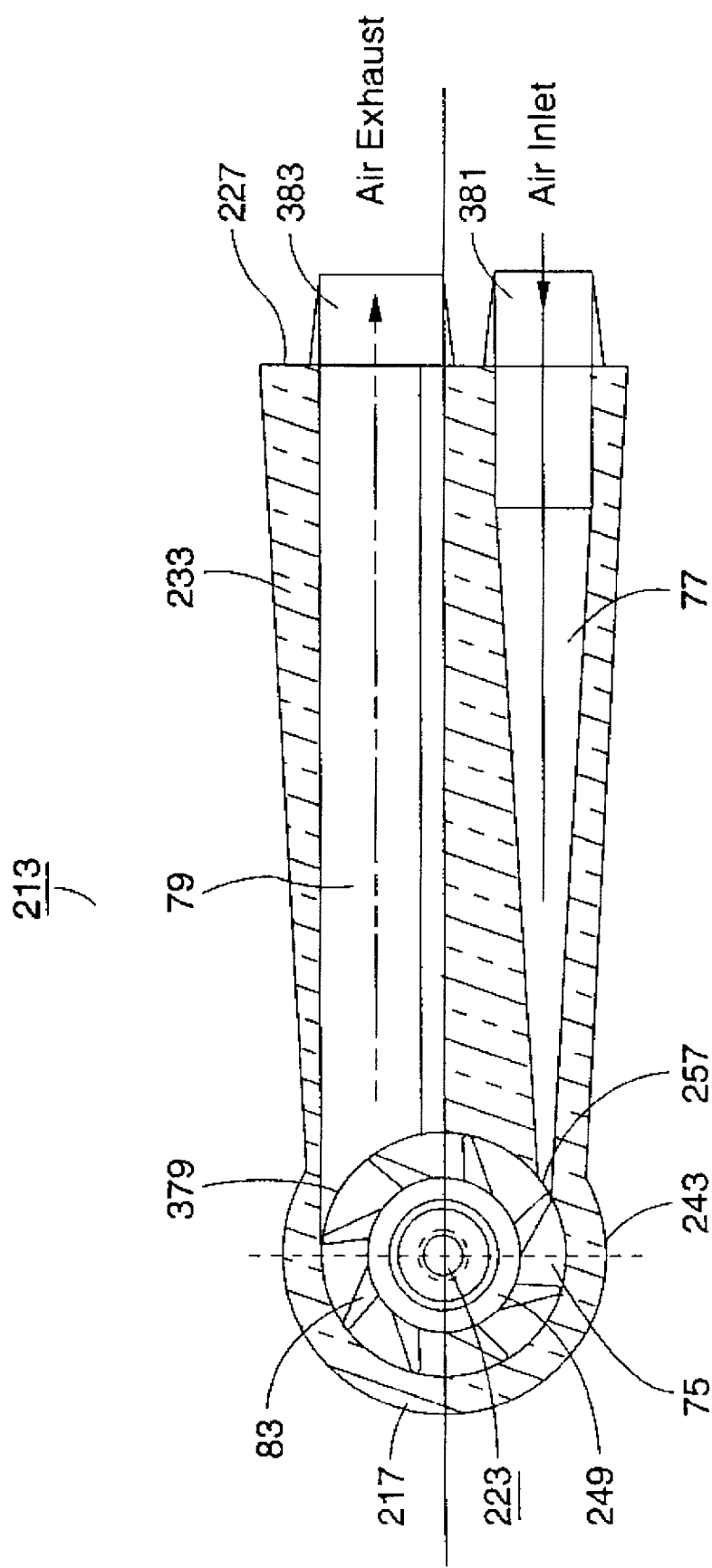
FIG. 15 is a top cross-sectional view of the head of FIG. 13.

The turbine portion 249 of the rotor 245 is integrally coupled to the shaft portion 247 and is located centrally within the cavity 75. A cylindrical blade mount 255 extends radially outward from the shaft portion 247 and is coupled to the shaft portion for rotation therewith between the upper and lower bearings 219 and 221. A plurality of turbine blades 83 are coupled to the turbine blade mount 255 and extend outward from the blade mount 255. The turbine blades 83 are positioned to receive air from an air inlet opening 257 in the housing 217. As shown in FIG. 15, the turbine blades 83 extend from the turbine blade mount 255 at an acute angle so the blades 83 are positioned to cup air injected into the cavity 75 through the air inlet 257. In a preferred embodiment, the rotor 245 is formed of a single piece of injection molded plastic. The plastic may be glass reinforced nylon for example produced by Hoescht Celanese 1500 FDA.

Referring back to FIGS. 13 and 14, the drill burr 101 is removably coupled to the shaft portion 247 of the rotor 245. The drill burr 101 may be a conventional, commercially available burr 101 used for dental drilling. The drill burr 101 has a shaft section 259 and a drill tip 261. The shaft section 259 fits within an inner bore 263 of the shaft portion 247 of the rotor 245 extending along the longitudinal axis of the shaft portion 247. The drill tip 261 is integrally coupled to the shaft section 259 outside the housing 217 of the head assembly 213 in a position for drilling operations.

Figure 18:
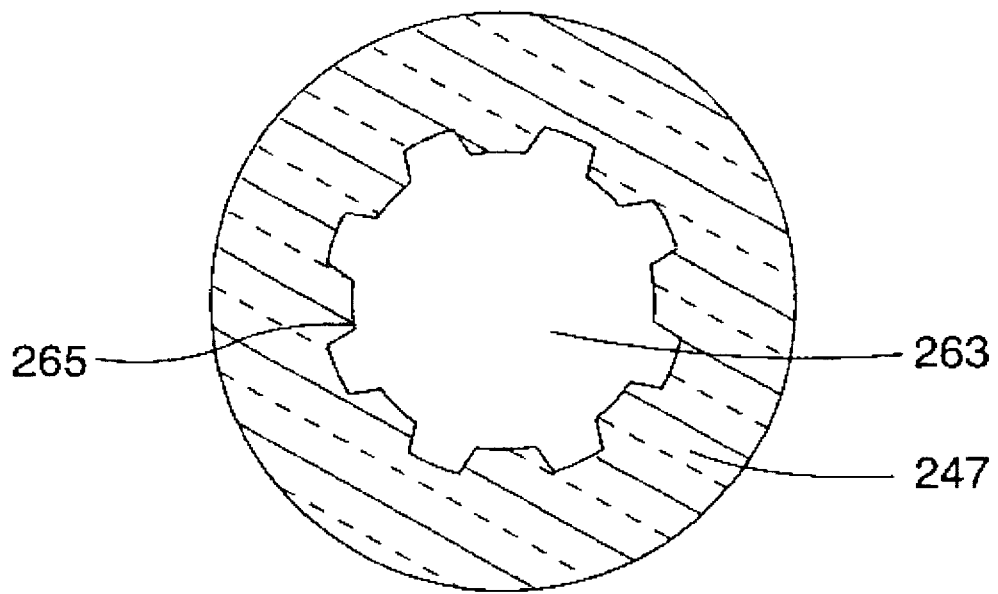
FIG. 18 is a cross-sectional view of the shaft as seen from lines 18—18 of FIG. 14.

As shown in FIG. 18, the shaft portion 247 of the rotor 245 has a plurality of splines 265 located extending radially inward into the inner bore 263. The drill burr 101 has a plurality of splines (not shown) located along a portion of the shaft section 259 extending radially outward from the shaft section 259 which frictionally fit in the gaps between the splines 265 of the splined inner bore 263 to secure the drill burr 101 within the shaft portion 247.

Referring to FIGS. 13, 14, 37 and 38, the rotor 245 is rotatably secured in the housing 217 by the upper and lower bearings 219 and 221. The upper and lower bearings 219 and 221 are comprised of a plurality of balls 269A and 269b, respectively, located in bearing cages 271A and 271B, respectively. Cage 271A is located between inner and outer races 273A and 275A respectively and cage 271B is located between inner and outer races 273B and 275B respectively. The inner races 273A and 273B are secured to the shaft portion 247 of the rotor 245 for rotation with the rotor. The outer races 275A and 275B are secured to the housing 217 to support the drill assembly 223 in the housing. The bearing cages 271A and 271B and the balls 269A and 269B located between the inner races 273A or 273B, respectively, and the outer races 275A or 275B, respectively, permit the inner races 273A, and 273B and the shaft 247 to rotate relative to the outer races 275A and 275B while permitting the outer races 275A and 275B to secure the rotor 245 in the housing 217.

Figure 37:
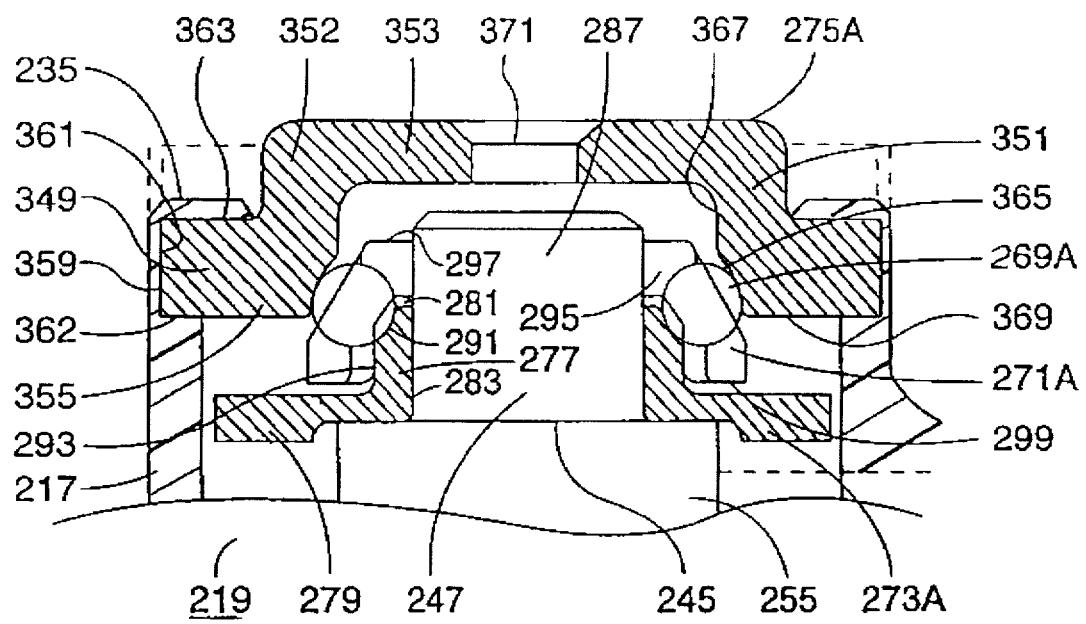
FIG. 37 is an enlarged side cross-sectional view of the head assembly of FIG. 13.
Figure 38:
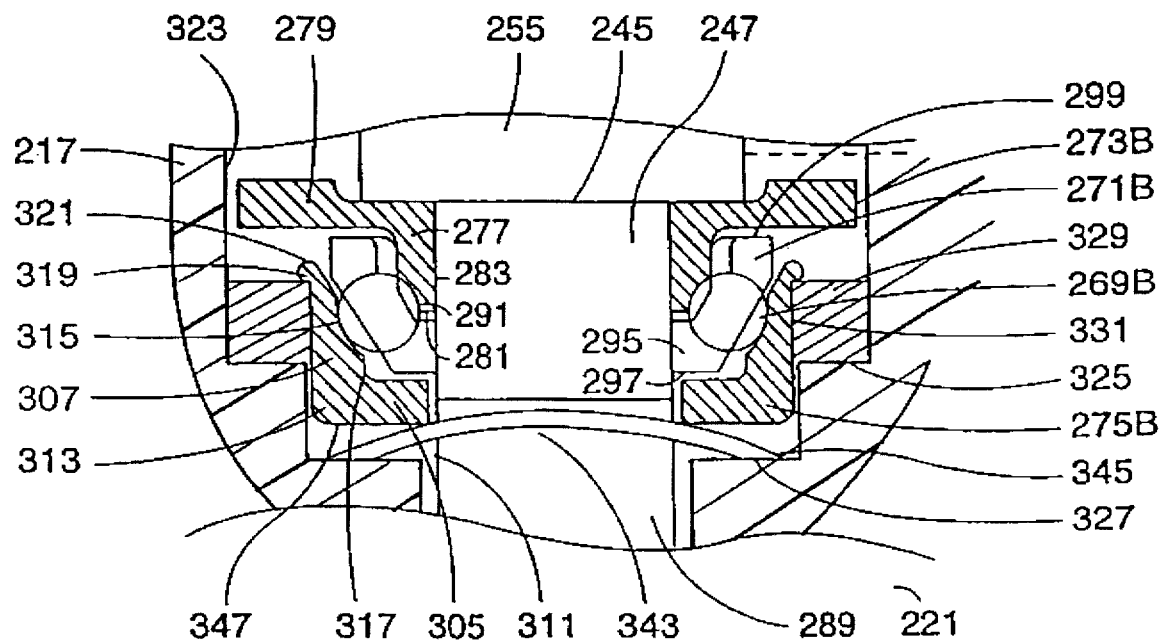
FIG. 38 is an enlarged side cross-sectional view of the lower bearings of the head assembly of FIG. 13.

As shown in FIGS. 14, 37 and 38, each inner race 273A and 273B has a circular wall 277 having a flanged end 279 and a race end 281. The inner surface 283 of the circular wall 277 of each race 273A and 273B extends about and defines an inner race aperture 285 which frictionally fits around the shaft portion 247 of the rotor 245 for rotation therewith. The inner race 273A of the upper bearing 219 is located around an upper portion 287 of the shaft 247 and the inner race 273B of the lower bearing 221 is located around a lower portion 289 of the shaft 247. The flanged end 279 of each inner race 273A and 273B is located abutting the turbine blade mount 255. The flanged ends 279 of each inner race 273A and 273B provide walls for the sides of the turbine blades 83 to better cup air injected into the cavity 75 through the air inlet 257. Due to the higher density of the metal used in the inner races 273A and 273B, significant additional inertia is provided to the spinning rotor assembly (rotor 245 and inner races 273A and 273B) by the flanged ends 279. Angled inner race surface 291 extends through the outer surface 293 of the circular wall 277 near the race end 281 of the wall 277 for receiving and seating the balls 269A or 269B of the bearing cage 271A or 271B, respectively. In a preferred embodiment, the inner races 273A and 273B are formed of precision made stainless steel.

Figure 16:
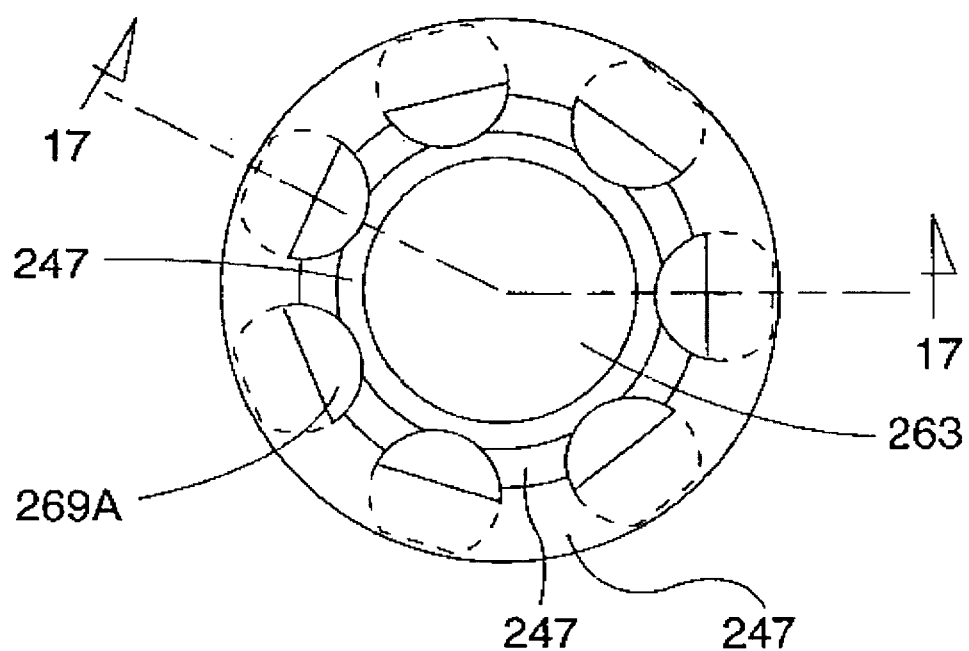
FIG. 16 is a top view of a bearing cage located about the shaft portion of the rotor in the head assembly.
Figure 17:
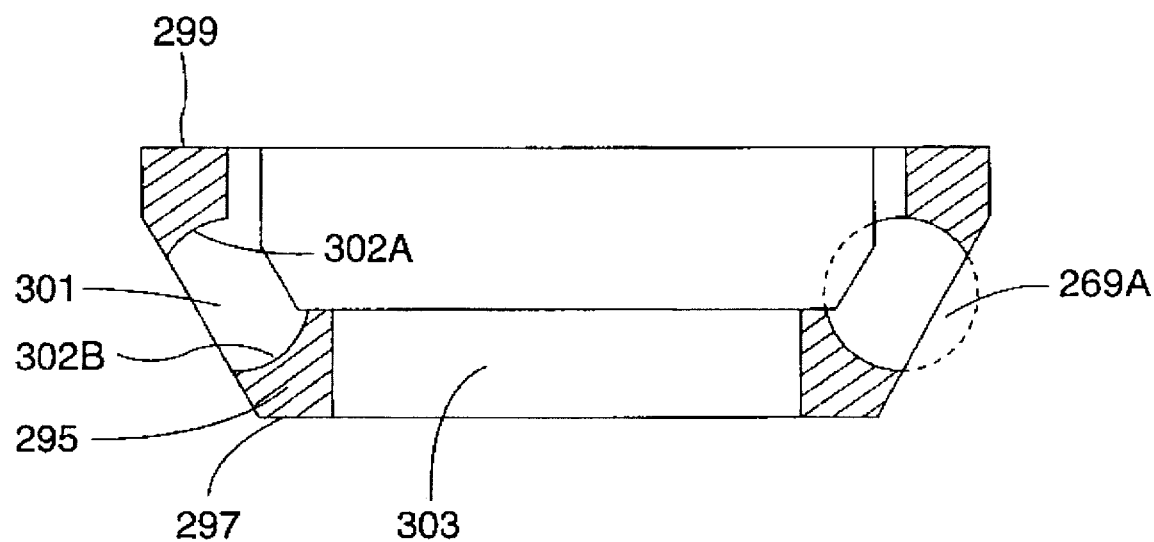
FIG. 17 is a side cross-sectional view of the bearing cage taken along lines 17—17 FIG. 16.

As shown in FIGS. 37 and 38, the bearing cages 271A and 271B position the balls 269A and 269B against the angled inner races surfaces 291 of the inner races 273A and 273B, respectively. Referring to FIGS. 16 and 17, each bearing cage 271A and 271B is formed of a cupped ting member 295 having a narrow end 297 and a wide end 299. A plurality of ball receiving apertures 301 having arcuate walls 302A and 302B for holding a ball bearing extend through the ring member 295 between the ends 297 and 299 symmetrically located about the ring member 295. The ball receiving apertures 301 retain the balls 269A or 269B in the ring member 295 while allowing the balls to rotate freely within the ring member.

Referring back to FIGS. 14, 37 and 38, each ring member 295 has a shaft receiving aperture 303 extending through the narrow end 297 of the ring 295 which frictionally fits around the shaft portion 247 of the rotor 245 so that the rings 295 may rotate with the shaft 247. The wide end 299 of the ring member 295 is located around the circular wall 277 of the inner race 273A or 273B adjacent the flanged end 279 of the inner race. The balls 269A and 269B are located against the angled inner race surfaces 291. When the ring member 295 is located around the inner race 273A or 273B. In a preferred embodiment, the bearing cages 271A and 271B are one piece injection molded plastic members and the balls 269A and 269B are hardened steel balls. The cages 271A and 271B may be formed of glass reinforced nylon for example produced by Hoescht Celanese 1500 FDA.

As shown in FIG. 13, the lower outer race 275B is secured in the cavity 75 near the bottom end 237 of the housing 217 and supports the balls 269B of the lower bearing cage 271B for rotation about the lower outer race. Referring again to FIGS. 14 and 38, the lower outer race 275B is a cap ring which is located around bearing cage 271B and comprises a radial wall 305 integrally coupled to an axial wall 307 which extends transverse to the radial wall. The radial wall 305 is located extending adjacent the narrow end 295 of the bearing cage 271B transverse to the shaft portion 247 of the rotor 245. The shaft 247 extends through a lower outer race aperture 309 located centrally in the radial wall 305. The diameter of the lower outer race aperture 309 is sufficiently large to separate the radial wall 305 from the shaft 247 by a gap 311 so that the lower outer race 275B is not affected by rotation of the shaft 247.

The axial wall 307 extends from an outer end 313 of the radial wall 305 parallel to the shaft 247 towards the flanged end 279 of the inner race 273B. The axial wall 307 is located adjacent the bearing cage 271B and contacts the balls 269B of the baring cage. A lower angled outer race surface 315 extends through the inner surface 317 of the axial wall 307 for receiving and seating the balls 269B of the bearing cage 271B. The lower angled outer race 315 is located opposite the angled inner race 291 of the inner race 273B across the ball receiving apertures 301 of the bearing cage 271B so that the lower angled outer race 315 and the angled inner race 291 cooperatively seat the balls 269B for rotation between them. In a preferred embodiment, the lower outer race 275B is formed of precision made stainless steel.

A lip 319 extends radially outward at outer end 321 of the axial wall 307 upon for supporting the lower outer race 275B in the housing 217. As shown in FIG. 38, the inner surface 323 of the housing 217 is stepped near the bottom end of the housing to form upper and lower shoulders 325 and 327. The upper shoulder 325 supports an elastomeric ring 329 thereon. Referring to FIGS. 13, 14 and 38, the elastomeric ring 329 extends about and abuts the outer surface 331 of the axial wall 307 of the lower outer race 275B. The lip 319 is located extending over the elastomeric ring 329 to secure the lower outer race 275B in the housing 217 such that the race 275B does not rotate. The elastomeric ring 329 absorbs vibration from the lower outer race 275B during operation of the drill handpiece 211.

Figure 40:
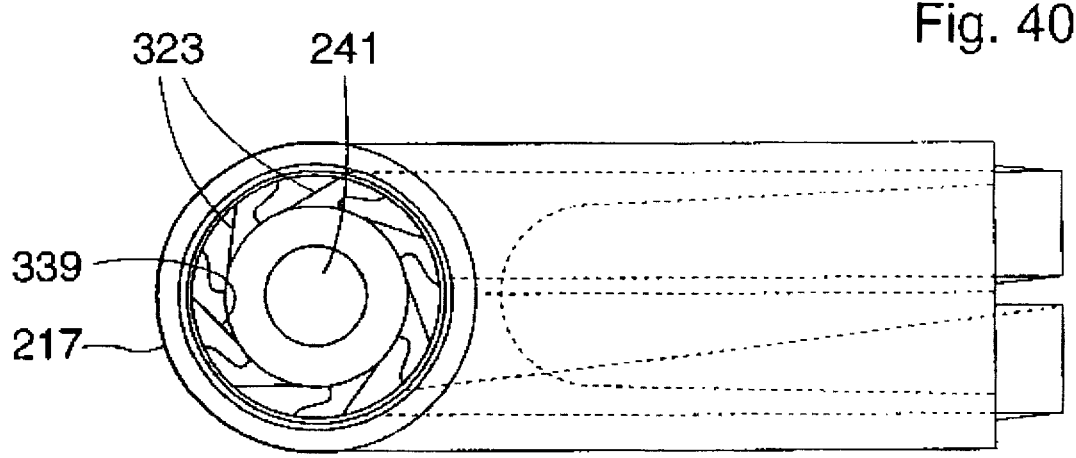
FIG. 40 is a top view of the head assembly incorporating wall structure support for the lower bearings.
Figure 41:
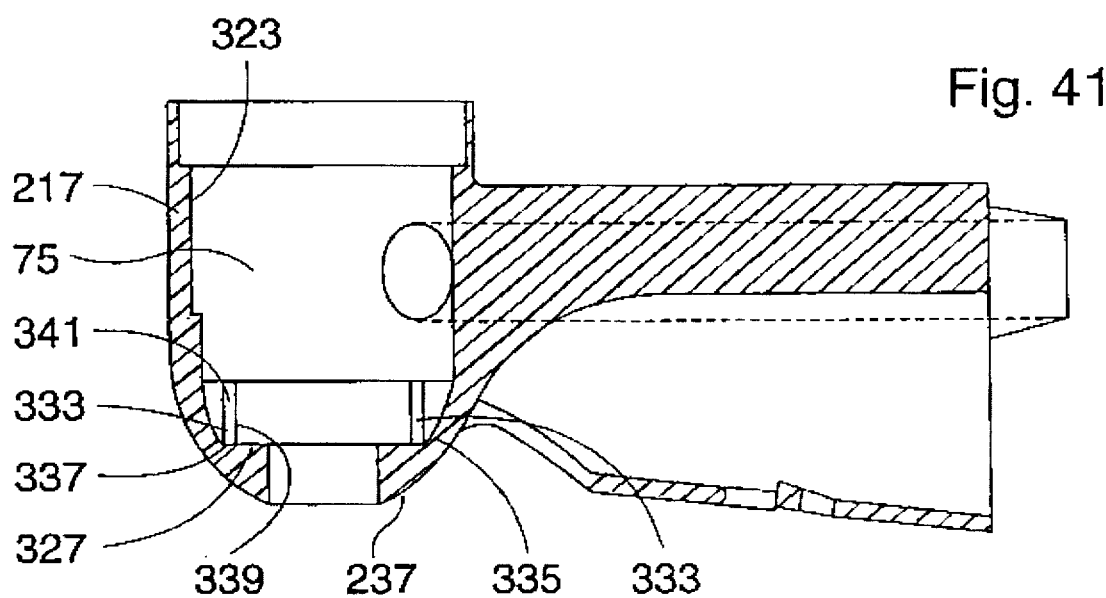
FIG. 41 is a side cross-sectional view of the head assembly of FIG. 40.

In another embodiment, as shown in FIGS. 40 and 41, the housing 217 is formed with a plurality of resilient or flexible wings 333 which are used to support the lip 319 of the lower outer race 275B. The housing 217 has a lower shoulder 327 located along the inner surface 323 of the housing near the bottom end 237 of the housing. An angled section 335 of the inner surface 323 of the housing 217 extends from outer edge 337 of the lower shoulder 327 widening the cavity 75 within the housing. A plurality of support wings 333 extends upwards from the junction of the angled section 335 and the lower shoulder 327. The outer surface 331 of the axial wall 307 of the lower outer race 275B abuts a portion of the inner surface 339 of each prong 333 and the lip 319 is located over the top of each prong 333 to support the lower outer race 275B in the housing 217. The support wings 333 absorb vibration from the lower outer race 275B during operation of the handpiece 211. The wings 333 take the place of the ting 329.

Referring back to FIGS. 13, 14 and 38, an annular spring washer 343 is located extending about the shaft 247 on the lower shoulder 327 in the inner surface 323 of the housing 217. The spring washer 343 is convexly bowed upwards extending from an outer edge 345 located abutting the inner surface 323 of the housing to engage a lower face 347 of the radial wall 305 of the lower outer race 275B. The spring washer 343 engages the radial wall 305 to maintain the lower outer race 275B in contact with the ball bearings 269B in the bearing cage 271B.

Referring now to FIGS. 14 and 37, the upper outer race 275A is secured near the top end 235 of the housing 217 seating the balls 269A of the bearing cage 271A in position for rotation about the upper outer race. The upper outer race 275A has an outer radial wall 349, an axial wall 351, and an inner radial wall 353 where the axial wall 351 is integrally coupled between the radial walls 349 and 353 extending transversely from an inner portion 355 of the outer radial wall 349 to an outer portion 357 of the inner radial wall 353. The inner wall 369 of the race 275A is seated on a shoulder 362 of the housing 217 with the outer edge 359 engaging the housing wall 361 and the top end 235 of the housing 217 is pressed or folded over to firmly hold the upper outer race 275A in the housing against the ball bearings 269A of bearing cage 271A. The upper race 275A does not rotate. The upper race 275A is formed of stainless steel.

The outer radial wall 349 of the upper outer race 275A extends radially inward from the wall 361 of the housing 217 to the axial wall 351. An upper angled outer race 365 is located extending from the inner face 367 of the axial wall 351 adjacent the bottom surface 369 of the outer radial wall 349 for receiving and seating balls 269A of the bearing cage 271A. The upper angled outer race 365 is positioned opposite the angled inner race 291 of the inner race 273A abutting balls 269A so that the upper angled outer race 365 and the angled inner race 291 cooperatively seat the balls 269A for rotation between them. The custom angular contact bearings provide improved concentricity and load bearing compared with the more traditional radial contact bearings.

The axial wall 351 extends upwards from the outer radial wall 349 away from the bearings cage 271A and inner race 273A to the inner radial wall 353. The inner radial walls 353 extends radially inward above the shaft portion 247 of the rotor 245. A burr removal aperture 371 extends centrally through the inner radial wall 353 aligned with the inner bore 263 of the shaft 247. The burr removal aperture 371 is sized to permit the end 461 of a burr removing tool 373 (See FIG. 39) to be inserted into the inner bore 263 of the shaft 247 through the aperture 371 and aperture 263A of shaft 247 to allow the burr to be pushed out of the tool by way of opening 241 and another one inserted therein by way of opening 241 if desired.

Figure 31:
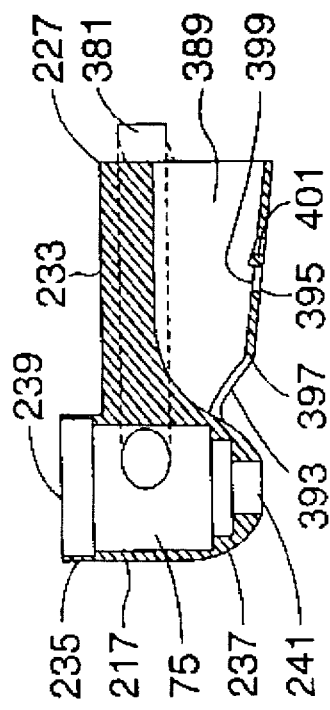
FIG. 31 is a side cross-sectional view of the head assembly of FIG. 13.

In inserting and securing the drill assembly 223 in the cavity 75, the housing wall 235 will be in the form of a cylinder as shown in FIG. 31. The drill assembly 223 of FIG. 14, then will be inserted into the cavity 75 with the spring washer 343 abutting against the wall 327 and the outer race 275A seated on shoulder 362. The wall 235 then will be folded and formed over to engage the top wall 363 of the race 275A to permanently secure the drill assembly 223 in the housing cavity. A drill burr 101 then may be inserted into the bore 263 by way of opening 241 for use. In the embodiment of FIGS. 40 and 41 the elastomer ring 329 will not be used.

Referring now to FIGS. 13 and 15, the neck 233 of the head assembly 213 is shown. The neck 233 is integrally coupled to a side 243 of the housing 217 and extends from the housing to the coupling end 227 of the head assembly 213. The neck 233 conducts air delivered by the handle 215 to and from the turbine portion 249 of the rotor 245 in order to drive the rotor to activate the drill handpiece 211. The neck 233 also receives and position the proboscis portion 229 of the handle 215 so that air, water, and light may be delivered to an area of drilling operations. Further, the neck snap locks with the handle 215 to secure the head assembly 213 to the handle 215. In a preferred embodiment, the neck 233 and housing 217 of the head assembly 213 are formed of a single piece of injection molded plastic. The plastic preferably is a polyester for example VALOX 210 HP made by G.E.

The neck 233 conducts air to and from the rotor 245 through an air inlet channel 77 and an air outlet or exhaust channel 79 to drive the rotor 245. The air inlet channel 77 and the air outlet channel 79 extend through an upper portion 375 of the neck 233 from the coupling end 227 to the cavity 75 in the housing 217. The air inlet channel 77 and air outlet channel 79 have openings 257 and 379, respectively, into the cavity 75 adjacent the turbine portion 249 of the rotor 245 so that air may be delivered to and removed from the cavity 75 adjacent the turbine blades 83 through the channels 77 and 79, respectively. The air inlet channel 77 narrows as it approaches the cavity 75 to increase the pressure of air delivered through the air inlet channel 77 to the rotor 245. The air outlet channel 79 has a continuous width, equal to the widest portion of the air inlet channel, through the length of the neck 233 to ensure that excessive air pressure does not build up within the cavity 75.

The air inlet channel 77 and the air outlet channel 79 extend through neck inlet and outlet coupling members 381 and 383, respectively, located protruding from the coupling end 227 of the head assembly 213. The inlet and outlet coupling members 381 and 383 are inserted into the air inlet and air outlet channels 385 and 387, respectively, of the handle 215 when the handle 215 and head assembly 213 are joined to provide sealed passages from channel 385 to channel 77 and from channel 387 to channel 79.

Referring now to FIGS. 13, 19, and 31–33, the neck cavity 389 extends from an inlet 391 through the lower portion 390 of the neck 233 below the air inlet and air outlet channels 77 and 79 from the coupling end 277 of the head assembly 213 to an outlet opening 393 located in the neck 233 adjacent to the housing 217 of the head assembly 213. The neck cavity 389 is shaped to matingly receive the proboscis portion 229 of the handle 215 through the coupling end 227 of the head assembly 213 when the handle 215 and head assembly 213 are joined. When this occurs the proboscis portion 229 of the handle 215 extends through the neck cavity 389 to the outlet opening 393. The outlet opening 393 is located close to the bottom end 237 of the housing 217 and is directed towards the drill burr 101 so that air, water, and light may be delivered to the drill burr 101 from the proboscis 229 through the outlet opening 393 when the handpiece 211 is being operated.

Figure 20:
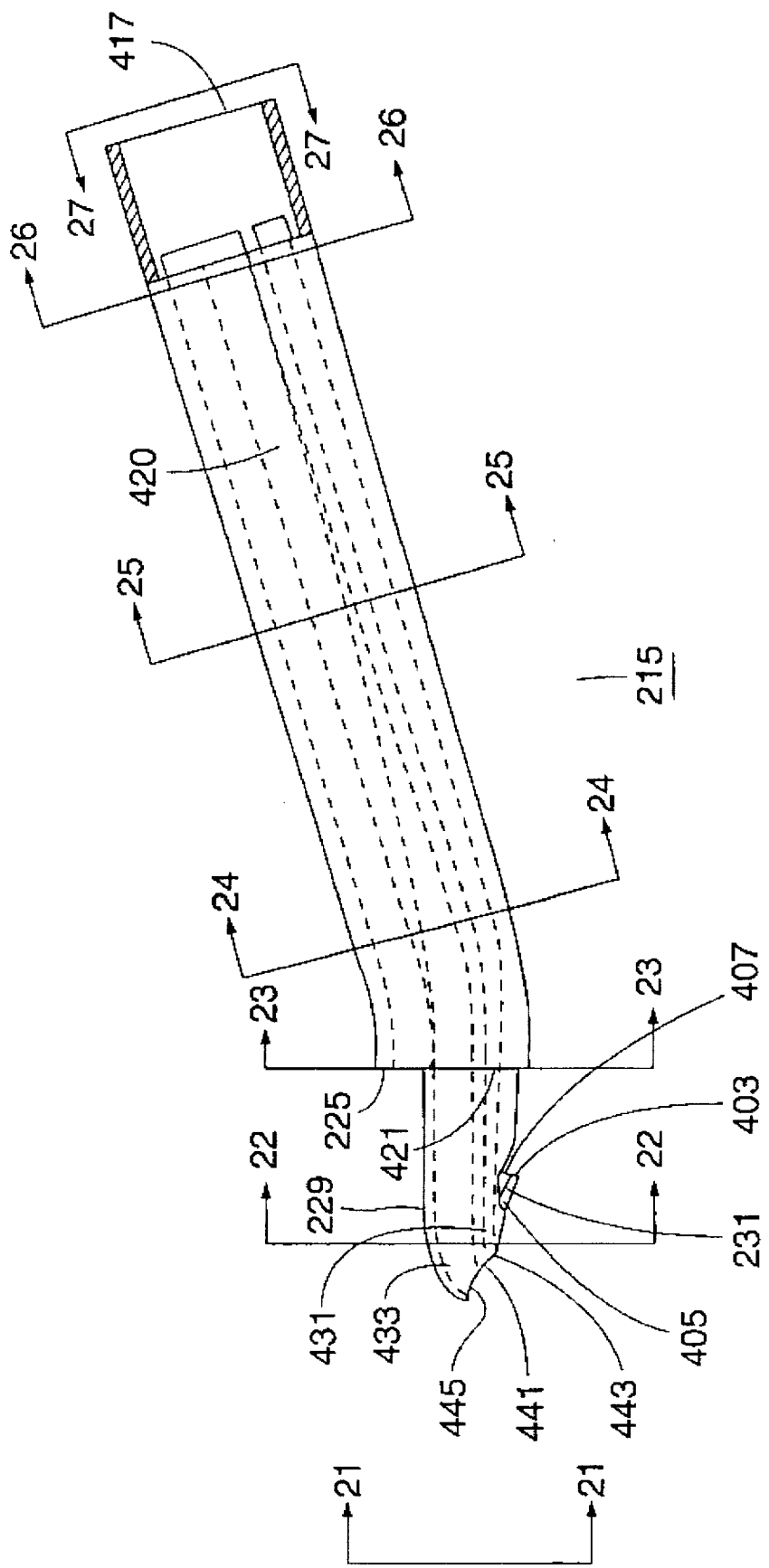
FIG. 20 is a side view of the handle used with the head of FIG. 13.
Figure 30:
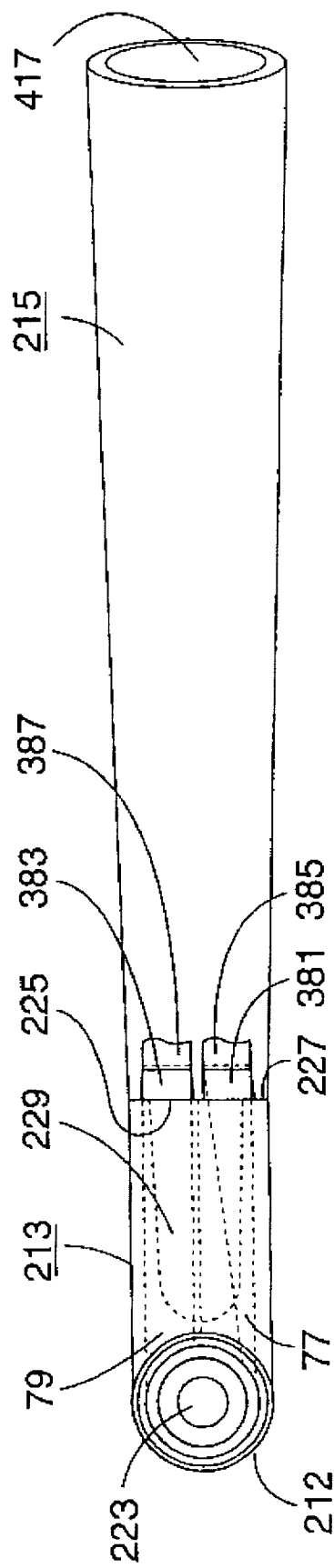
FIG. 30 is the head of FIG. 13 coupled to the handle of FIG. 20.

Referring also to FIGS. 20 and 29, a locking section 395 is formed through the bottom wall 397 of the neck 233 between the outlet opening 393 and the coupling end 227 of the head assembly 213. The locking section 395 cooperatively interacts with the protuberance 231 extending from the proboscis 229 of the handle 215 to snap lock the disposable head assembly 213 onto the handle 215. The locking section 395 has a U-shaped opening 399 centered and formed through the bottom wall 397 of the neck 233 with the legs of the "U" facing the coupling end 227 of the head assembly 213. A resilient flap 401 is formed by the U-shaped opening 399 between the legs of the "U". The bight 339B of the U-shaped opening 399 receives the protuberance 231 of the proboscis 229 of the handle 215 and the flap 401 engages the back end 403 of the protuberance 231 to lock the head assembly 213 and handle 215 together.

As shown in FIGS. 20 and 29, the protuberance 231 has a gently outwardly sloped front portion 405 and a cleft 407 located at the back end 403 of the protuberance 231. Referring now to FIGS. 13, 19–20, and 31–33, when the proboscis 229 of the handle 215 in inserted into the neck cavity 389 of the head assembly 213 the front potion 405 of the protuberance 231 pushes the free end 409 of the flap 401 outward as the front portion 405 is moved over the flap 401. As the handle 215 reaches its fully inserted position in the head assembly 213 the front portion 405 of the protuberance 231 slips into the U-shaped opening 399 and the free end 409 of the flap 401 snaps into the cleft 407 at the back end 403 of the protuberance 231, locking the handle 215 and head assembly 213 together. The inner surface 411 of the flap 401 is angled to extend inwards into the neck cavity 389 relative to the inner surface 413 of the bottom wall 397 of the neck 233 to ensure that the flap 401 firmly engages the cleft 407 when the protuberance 231 is located in the U-shaped opening 399.

After the disposable head assembly 213 has been used, the flap 401 may be broken off to unlock the head assembly 213 from the handle 215. A flap removal aperture 415 is centered in the flap 401 extending through the flap 401. The end 461 of the burr removing tool 373 (See FIG. 39) may be inserted into the flap removal aperture 415. After the burr removing tool 373 is located in the flap removal aperture 415 the burr removing tool may be twisted or moved to snap the flap 401 off of the head assembly 213. The protuberance 231 may then be removed from the U-shaped opening 399 and the handle 215 retracted from the head assembly 213. The used head assembly 213 is discarded.

Referring now to FIGS. 20–30, the handle 215 of the handpiece is an elongated metal member having an inlet end 417 and an outlet end 225. The inlet end 417 may be coupled to compressed air, water and light sources, and the outlet end 225 is removably coupled to the disposable head assembly 213. Compressed air is delivered to and removed from the head assembly 213 through the outlet end 225 to control operation of the drill handpiece 211. The proboscis portion 229 of the handle 215 is a metal tube narrower than the body 420 of the handle which is integrally coupled to a lower portion 421 of the outlet end 225 of the handle extending forward of the outlet end 225 to a nozzle end 441. As described above, the protuberance 231 extending from the bottom 423 of the proboscis 229 locks the handle 215 together with the head assembly 213. Air, water, and light are delivered to the outlet opening 393 in the head assembly 213 through the proboscis 229 to aid in drilling operations (See FIGS. 32–33).

Air inlet and exhaust channels 385 and 387 extend side by side through a top portion 422 of the handle 215 from the inlet end 417 to the outlet end 225. Referring to FIG. 23, a one way valve 66 is located in the air inlet channel 385 of the handle 215 at the outlet end 225 of the handle to prevent foreign material form being sucked back into the handle. The valve 66 allows fluid to flow only out of the channel 385 into the channel 77. The air inlet channel 385 of the handle 215 delivers the air to the air inlet channel 77 of the head assembly 213, which conducts the air to the cavity 75 to drive the drill assembly 223. The air exits the cavity 75 through the air outlet or exhaust channel 79 in the head assembly 213, which conducts the air to the air outlet or exhaust channel 387 in the handle 215. The air outlet or exhaust channel 387 in the handle 215 delivers the air to the end 417 of the handle where the air is exhausted from the handle.

As shown in FIGS. 20 and 23–26, the exterior shape of the handle has a somewhat triangular cross section in the region it is gripped by the dentist near and rearward of the end 225. The cross section gradually changes to a circular cross section at the end where it mates with a connector to the dental stand. The triangular shape of the handle is designed to match the cross section of the mating head to provide a smooth surface where the surface of the apparatus may contact the mouth of the patient. The generally triangular cross section also promotes a better grip of the handle and consequently better control of the dental burr. It also has a more natural feel resulting in less fatigue to the dentist.

As shown in FIGS. 21–27 and 36, a mist channel 431 and a light pipe channel 433, as well as the air inlet channel 385 and the air outlet channel 387, extend through the handle 215 form the inlet end 417 to the outlet end 225 of the handle. The light pipe channel 433 is centered in the handle 215 extending beneath the air inlet and air outlet channels 385 and 387. The mist channel 431 is located extending through the lower portion 435 of the handle 215 beneath the light pipe channel 433. A water pipe 437 extends centrally through the mist channel 431 and is coupled to a water source at the inlet end 417 of the handle 215. The mist channel 431 is coupled to the compressed air source so that air may be conducted through the mist channel 431 about the water pipe 437. A light pipe 439 carrying conventional fiber optics for conducting light extends through the light pipe channel 433. The light pipe 439 and its fiber optics are coupled to a fiber optic light source beyond the inlet end 417 of the handle 215.

As shown in FIGS. 20, 21, 29 and 36, the mist channel 431 and light pipe channel 433 together with the water pipe 437 and the light pipe 439, respectively, extend through the proboscis 229 of the handle to the nozzle end 441 of the proboscis. The mist channel 431 and the light pipe channel 433 extend to a mist opening 443 and a light opening 445, respectively, at the nozzle end 441 of the proboscis 229. The light pipe 439 extends through the light pipe channel 433 to a position adjacent the light opening 445 so that light may be directed through the light opening. The water pipe 437 terminates slightly inward from the mist opening 443 so that air and water directed through the mist channel 431 may combine to form a mist which may be directed out of the mist opening 443. The nozzle end 441 of the proboscis 229 is angled downwards with respect to the proboscis and the body 420 of the handle 215 so that an air-water mist and light may be projected out of the mist opening 443 and the light opening 445 through the outlet opening 393 directed towards the drill burr 101 when the proboscis is secured in the neck cavity 389 of the head assembly 213 (See FIGS. 32 and 33).

As shown in FIGS. 34 and 35, the inlet end 417 of the handle 215 may be securely attached to a conduit 429 of a conventional dental stand so that air, water and light may be provided to the handle from the stand. The conduit 429 has channels 385C, 387C, 431c, and 433c which conform with channels 385, 387, 431, 433 respectively of the handle. Connecting tubes 385CC, 387CC, 431CC, and 433CC extend beyond the wall 417W of the handle and can be inserted in the channels 385C, 387C, 431C and 433C respectively when the end 429E of the conduit 429 is inserted into the opening 417A of the handle and pushed against the end wall 417W of the handle. Sealed passageways 385–385C, 387–387C, 431–431C and 433–433C thus are formed. In one embodiment, the water pipe 437 and light pipe 439 extend out of the channels 431C and 433C and have lengths sufficient such when the end 429E of the conduit 429 abuts against the wall 417W, the pipes 437 and 439 will extend through the passages 431 and 433 of the handle to the nozzle end 441C.

An annular coupling fixture 441 is located around the conduit 429 and has threads 441T adapted to be screwed to the threads 417T of the handle 215 to securely couple the handle 215 to the conduit 429.

The channels 431C and 433C will be coupled to sources of compressed air; the pipe 437 will be coupled to a source of water; and the light pipe 439 will be coupled to a controllable source of light. The pipe or tube 437 may be formed of a suitable plastic.

Figure 39:
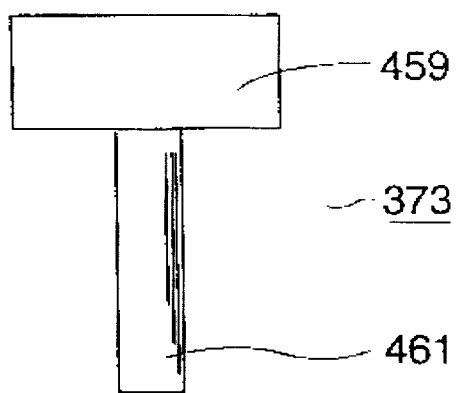
FIG. 39 is a side view of a tool for use with the invention.

As shown in FIG. 39, a burr removing tool 373 is provided for the handpiece 211. The burr removing tool 373 may be used to remove drill burrs 101 from the head assembly 213 so that drill burrs may be interchanged in the head assembly, and the burr removing tool 373 may be used to break the flap 401 off of the head assembly 413 to unlock the handle 215 from the head assembly 213. The tool 373 had a head portion 459 coupled to a cylindrical shank 461 which extends transverse to the head portion 459. The cylindrical shank 461 has a diameter sized to fit through the inner bore 263A, 263 of the shaft 247 of the rotor 245 and through the flap removal aperture 415 of the flap 401. In order to remove a drill burr 101 from the head assembly 213 with the tool 373, the head 459 of the tool 373 may be grasped and the shank 461 of the tool inserted into the inner bore 263A, 263 of the shaft 247 by way of the aperture 371 in the upper bearings 219. The shank 461 is located adjacent the drill burr 101 in the shaft 247 and force is applied against the drill burr 101 to dislodge the burr 101 from the head assembly 213. In order to break the flap 401 to unlock the head assembly 213 from the handle 215 the shank 461 is located in the flap removal aperture 415 and the flap 401 is twisted with the tool 373 until the flap 401 snaps away from the head assembly 413.

Figure 42:
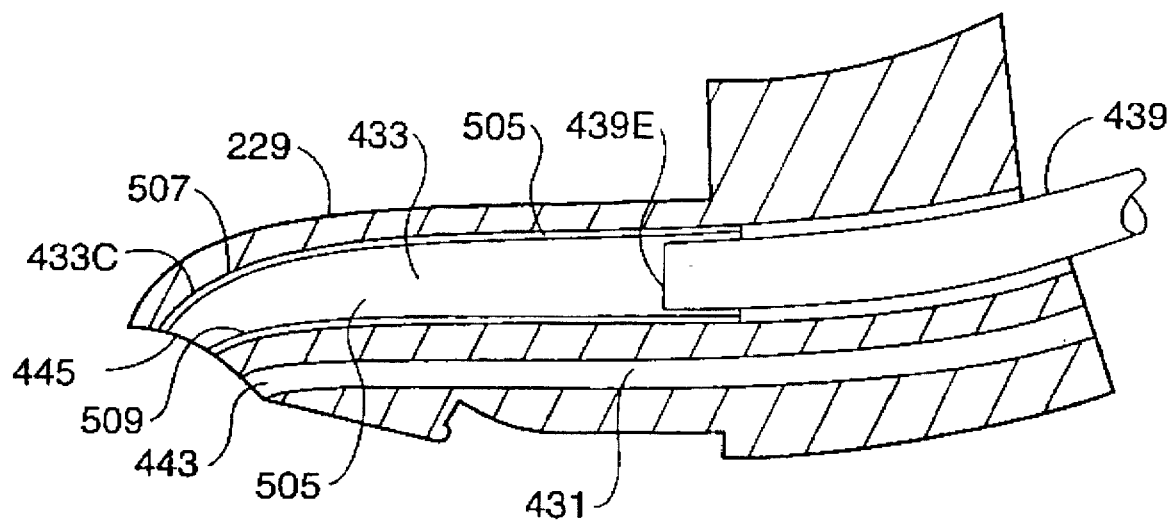
FIG. 42 is an enlarged partial cross-sectional view of the handle of FIG. 20 showing internal construction of the handle nozzle.
Figure 43:
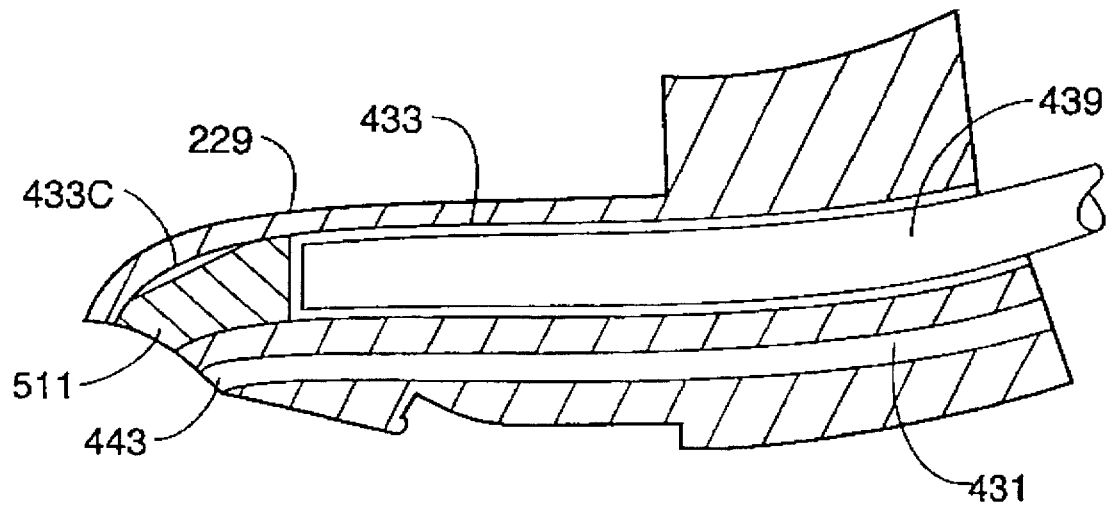
FIG. 43 is an enlarged partial cross-sectional view of the handle of FIG. 20 showing another embodiment for the light pipe termination.

FIGS. 42 and 43 illustrate embodiments wherein the light pipe is terminated within the nozzle cavity 433. FIG. 42 shows the light pipe 439 terminating within the internal cavity 433 of the nozzle or proboscis 229. The internal nozzle cavity 433 may be made optically reflective in the region 505, for example by applying a finish 507 of electroless nickel 507, such that the light exiting the light pipe 439 reflects off of the reflective internal walls 509 ultimately shinning through nozzle orifice 445 towards the tip of the dental burr. FIG. 43 shows the light pipe 439 terminating adjacent to an optically transparent lens 511, for example made of clear polycarbonate. This lens may function as an internal reflector for the light exiting the light pipe 439, reflecting the light through the nozzle orifice 445.

The purpose of terminating the light pipe 439 short of the orifice or opening 445 of the light pipe passage 433 is that generally a light pipe is formed of a bundle of fiber optic strands with their ends bound together with a surrounding metal ferrule. It is difficult to have the fiber optics bundle with the metal ferrule turn the corner of the curved portion 433C of the passage 433 and seat properly in the curved portion. With the embodiments of FIGS. 42 and 43, the end 439E of the fiber optics bundle with the surrounding ferrule terminates before reaching the curved portion 433C. The embodiment of FIG. 43 has advantages over that of FIG. 42 in that the lens 511 will prevent dust and particles from entering the passage 433.

The foregoing disclosure and the showings made in the drawings are merely illustrative of the principles of this invention and are not to be interpreted in a limiting sense.

We claim:

1. A disposable head assembly for a dental drill, comprising:

a housing forming a head with first and second opposite ends and a neck extending from a side of said head between said first and second opposite ends to a coupling end, a head cavity formed in said head with first and second openings at said first and second ends respectively leading to said head cavity, a shaft having first and second ends with said second end of said shaft being adapted to have a drill burr coupled thereto, a turbine coupled to said shaft between said first and second ends of said shaft, said shaft and said turbine being located in said head cavity with said second end of said shaft located near said second opening at said second end such that when a drill burr is coupled to said second end of said shaft, said drill burr extends out of said second opening at said second end of said head, first and second bearing means located in said cavity for supporting said shaft and said turbine for rotation, said first bearing means comprising a first outer bearing member coupled to said housing at said first end of said head, a first inner bearing member coupled to said first end of said shaft, and bearing means located between and engaging said first outer bearing member and said first inner bearing member, said first outer bearing member comprising an annular side wall having a first end with an outward extending flange and a second end coupled to a circular shaped wall defining a cavity on an inner side for receiving said bearing means located between said first outer bearing member and said first inner bearing member and said first end of said shaft, said circular shaped wall having said first opening formed therethrough with said first opening having a size less than the size of said first end of said shaft, said first end of said housing being folded to engage the outer surface of said flange to secure said first outer bearing member to said housing, said second bearing means comprising a second outer bearing member coupled to said housing at said second end of said head, a second inner bearing member coupled to said second end of said shaft, and bearing means located between and engaging said second outer bearing member and said second inner bearing member, an air inlet channel and an air exhaust channel extending from said coupling end of said neck and leading to said head cavity for directing air onto said turbine and from said head cavity for rotating said turbine, and a neck cavity extending from said coupling end of said neck to an outlet opening located close to and directed toward a drill burr when extending out of said second opening at said second end of said head.

2. The disposable head assembly of claim 1, wherein:

said first inner bearing member and said second inner bearing member extend radially outward to positions near the inner wall of said housing defining said head cavity for minimizing the passage of air from between the outer ends of said first and second inner bearing members and the inner wall of said housing.

3. The disposable head assembly of claim 1, comprising:

a first ball bearing cage with first ball bearings located between said first inner bearing member and said first outer bearing member with said first ball bearings engaging said first inner and outer bearing members at positions such that the points of engagements define a cone having an apex at the axis of said shaft, a second ball bearing cage with second ball bearings located between said second inner bearing member and said second outer bearing member with said second ball bearings engaging said second inner and outer bearing members at positions such that the points of engagements define a cone having an apex at the axis of said shaft.

4. The disposable head assembly of claim 2, comprising:

a first ball bearing cage with first ball bearings located between said first inner bearing member and said first outer bearing member with said first ball bearings engaging said first inner and outer bearing members at positions such that the points of engagements define a cone having an apex at the axis of said shaft, a second ball bearing cage with second ball bearings located between said second inner bearing member and said second outer bearing member with said second ball bearings engaging said second inner and outer bearing members at positions such that the points of engagements define a cone having an apex at the axis of said shaft.

5. The combination of a disposable head assembly for a dental drill and a handle; comprising:

a housing forming a head with first and second opposite ends and a neck extending from aside of said head between said first and second opposite ends to a coupling end, a head cavity formed in said head with first and second openings at said first and second ends respectively leading to said head cavity, a shaft having first and second ends with said second end of said shaft being adapted to have, a drill burr coupled thereto, a turbine coupled to said shaft between said first and second ends of said shaft, said shaft and said turbine being located in said head cavity with said second end of said shaft located near said second opening at said second end of said head such that when a drill burr is coupled to said second end of said shaft, said drill burr extends out of said second opening at said second end of said head, first and second bearing means located in said cavity for supporting said shaft and said turbine for rotation, said first bearing means comprising a first outer bearing member coupled to said housing at said first end of said head, a first inner bearing member coupled to said first end of said shaft, and bearing means located between and engaging said first outer bearing member and said first inner bearing member, said first end of said housing being formed to engage and secure said first outer bearing member to said housing, said second bearing means comprising a second outer bearing member coupled to said housing at said second end of said head, a second inner bearing member coupled to said second end of said shaft, and bearing means located between and engaging said second outer bearing member and said second inner bearing member, an air inlet channel and an air exhaust channel extending from said coupling end of said neck and leading to said head cavity for directing air onto said turbine and from said head cavity for rotating said turbine, a neck cavity extending from said coupling end of said neck to an outlet opening located close to and directed toward a drill burr when extending out of said second opening at said second end of said head, a handle adapted to be releasably coupled to said neck of said head assembly, said handle having a proboscis adapted to be located in said neck cavity by way of said coupling end of said neck and to be located next to said outlet opening of said neck cavity when said handle is coupled to said head assembly, said handle having an air inlet channel and an air exhaust channel extending from an inlet end of said handle to an outlet end portion adapted to be coupled to said air inlet channel and said air exhaust channel respectively of said neck at said coupling end of said neck when said handle is coupled to said neck of said head assembly, said handle having at least two conduits extending from said inlet end of said handle to said proboscis at least one of which is employed for directing a fluid through said outlet opening of said neck cavity when said handle is coupled to said neck.

6. The head assembly and handle of claim 5, comprising:

a U-shaped opening formed through the wall of said neck between said outlet opening of said cavity of said neck and said coupling end of said neck forming a resilient flap having a free end located closer to said outlet opening of said cavity of said neck than said coupling end of said neck, said handle having a protuberance extending therefrom near said proboscis end such that when said proboscis is inserted into said cavity of said neck, said protuberance is able to push said flap outward to allow said protuberance to be located between said free end of said flap and said outlet opening of said cavity of said neck to secure said handle to said neck of said head.

7. The head assembly and handle of claim 6, wherein:

said housing of said head assembly is formed of a plastic material whereby said flap may be broken to allow said handle to be removed from said head assembly to allow disposal of said head assembly.

8. The head assembly and handle of claim 6, comprising:

a one way valve located in said inlet air channel of said handle to allow flow therethrough only from said inlet end of said handle to said outlet portion.

9. The head assembly and handle of claim 5, comprising:

a light pipe opening extending from said inlet end of said handle to said proboscis for receiving a light pipe for directing a beam of light through said outlet opening of said neck cavity toward said drill burr when in place when said handle is coupled to said neck.

10. A disposable head assembly and a handle for a dental drill, comprising:

a housing forming a head with first and second opposite ends and a neck extending from a side of said head between said first and second opposite ends to a coupling end, a head cavity formed in said head with first and second openings at said first and second ends respectively leading to said head cavity, a shaft having first and second ends, a turbine coupled to said shaft between said first and second ends of said shaft with said second end of said shaft being adapted to have a drill burr coupled thereto, said shaft and said turbine being located near said second opening at said second end of said head such that when a drill burr is coupled to said second end of said shaft, said drill burr extends out of said second opening at said second end of said head, first and second bearing means located in said cavity for supporting said shaft and said turbine for rotation, an air inlet channel and an air exhaust channel extending from said coupling end of said neck and leading to said head cavity for directing air onto said turbine and from said head cavity for rotating said turbine, and a neck cavity extending from said coupling end of said neck to an outlet opening located close to and directed toward said drill burr when extending out of said second opening of said second end of said head, said handle being adapted to be releasably coupled to said neck of said head assembly, said handle having a proboscis adapted to be located in said neck cavity by way of said coupling end of said neck and to be located next to said outlet opening of said neck cavity when said handle is coupled to said head assembly, said handle having an air inlet channel and an air exhaust channel extending from an inlet end of said handle to an outlet end portion adapted to be coupled to said air inlet channel and said air exhaust channel respectively of said neck at said coupling end of said neck when said handle is coupled to said neck of said head assembly, said handle having at least two conduits extending from said inlet end of said handle to said proboscis at least one of which is employed for directing a fluid through said outlet opening of said neck cavity when said handle is coupled to said neck.

11. The head assembly and handle of claim 10, comprising:

a U-shaped opening formed through the wall of said neck between said outlet opening of said cavity of said neck and said coupling end of said neck forming a resilient flap having a free end located closer to said outlet opening of said cavity of said neck than said coupling end of said neck, said handle having a protuberance extending therefrom near said proboscis end such that when said proboscis is inserted into said cavity of said neck, said protuberance is able to push said flap outward to allow said protuberance to be located between said free end of said flap and said outlet opening of said cavity of said neck to secure said handle to said neck of said head.

12. The head assembly and handle of claim 11, wherein:

said housing of said head assembly is formed of a plastic material whereby said flap may be broken to allow said handle to be removed from said head assembly to allow disposal of said head assembly.

13. The head assembly and handle of claim 10, comprising:

a light pipe opening extending from said inlet end of said handle to said proboscis for receiving a light pipe for directing a beam of light through said outlet opening of said neck cavity toward said drill burr when in place when said handle is coupled to said neck.

14. The head assembly and handle of claim 10, comprising:

a one way valve located in said inlet air channel of said handle to allow flow therethrough only from said inlet end of said handle to said outlet portion.

15. A high speed dental apparatus, comprising:

a reusable dental handpiece handle having a body and a neck;

a disposable head assembly removably coupled to said neck of said handle, said disposable head assembly having a housing forming a cavity;

a turbine rotatably located in said cavity in said housing of said head assembly;

a burr coupled to said turbine, said burr being located in said cavity and extending out of said housing of said head assembly;

a plurality of bearings located between and rotatably contacting said turbine and said housing;

said burr is removably coupled to a shaft of said turbine within said housing of said head assembly;

an air conduit extending from an end of said handle into said handle and into said head assembly, said air conduit extending into said housing of said head assembly to said cavity, said air conduit being located to direct air from an air source against said turbine in said cavity for rotating said turbine;

an exhaust conduit extending from said cavity adjacent said turbine through said housing of said head assembly into said handle, through said handle to said end of said handle, said exhaust conduit being located to exhaust air from said cavity through said end of said handle;

a one way valve located in said air conduit in said neck of said handle to allow air flow only from said air conduit to said cavity.

16. The dental apparatus of claim 15, further comprising:

a nozzle integrally coupled to said neck of said handle and extending away from said handle, said nozzle having a passage extending therethrough from a nozzle end through said neck of said handle, said nozzle end having a nozzle aperture extending therethrough and communicating with said passage;

said housing of said head assembly has a nozzle receptacle extending therethrough, said nozzle being removably located therein, where said housing has a housing aperture extending therethrough adjacent said burr, said housing aperture communicating with said nozzle receptacle and being located adjacent said nozzle aperture through said nozzle end;

a water conduit, said water conduit extending through said handle into said passage in said nozzle and extending through said passage to said nozzle end, said water conduit being located at said nozzle end to dispense water through said nozzle and housing apertures;

said air conduit is defined as a first air conduit;

a second air conduit, said second air conduit extending through said handle into said passage in said nozzle and extending through said passage to said nozzle end, being located at said nozzle end to direct compressed air from a compressed air source through said nozzle and housing apertures;

fiber optic connectors extending through said handle into said passage in said nozzle and extending through said passage to said nozzle end, said fiber optic connectors being located adjacent said nozzle and housing apertures, said fiber optic connectors being capable of illuminating said burr through said nozzle and housing apertures.

17. The high speed dental apparatus of claim 16, further comprising:

a connector prong integrally coupled to said housing of said head assembly at an end of said housing, above said nozzle receptacle, said connector prong being removably coupled to said neck of said handle.

18. A high speed dental apparatus, comprising:

a reusable dental handpiece handle having a body and a neck;

a nozzle coupled to said neck extending away from said handle, said nozzle having a passage extending therethrough from a nozzle end through said neck of said handle, said nozzle end having a nozzle aperture extending therethrough and communicating with said passage;

a removable head assembly having a drill head and connecting portion, said head assembly being removably coupled to said neck of said handle at an end of said connecting portion, said connecting portion extending between said handle and said drill head;

said connecting portion having a nozzle receptacle extending therethrough, said nozzle being removably located therein, where said connecting portion has a housing aperture extending therethrough adjacent said nozzle aperture through said nozzle end;

a water conduit extending through said handle into said passage in said nozzle and extending through said passage to said nozzle end, said water conduit being located at said nozzle end to dispense water from a water source through said nozzle and housing apertures;

a burr extending out of said drill head;

means for rotating said burr located within said drill head;

fiber optic means extending through said handle into said passage in said nozzle and extending through said passage to said nozzle end, said fiber optic means being located adjacent said nozzle and housing apertures, said fiber optic means being capable of illuminating said burr through said nozzle and housing apertures;

a first air conduit extending from an end of said handle through said handle and into said head assembly, said first air conduit extending into said connecting portion of said head assembly to said drill head, said first air conduit being located to direct air from an air source against said means for rotating said burr;

a second air conduit extending through said handle into said passage in said nozzle and extending through said passage to said nozzle end, said second air conduit being located to direct air from an air source through said nozzle and housing apertures;

a one way valve located in said first air conduit in said neck of said handle to allow air flow only from said air conduit to said head assembly.

19. The dental apparatus of claim 18, further comprising:

a plurality of bearings located between and rotatably contacting said drill head of said head assembly and said means for rotating said burr;

a connector prong integrally coupled to said connecting portion of said head assembly at an end of said connecting portion, said connector prong being located above said nozzle receptacle and said connector prong being removably coupled to said neck of said handle, said burr is removably coupled to a shaft attached to said means for rotating said burr.

20. A high speed dental apparatus, comprising:

a reusable dental handpiece handle having a body and a neck;

a disposable head assembly removably coupled to said neck of said handle, said disposable head assembly having a housing forming a cavity;

a turbine rotatably located in said cavity in said housing of said head assembly;

a burr coupled to said turbine, said burr being located in said cavity and extending out of said housing of said head assembly;

an air conduit extending from an end of said handle through said handle and into said head assembly, said air conduit extending through said housing of said head assembly to said cavity, said air conduit being located to direct compressed air from a compressed air source against said turbine in said cavity for rotating said turbine and said burr;

a one-way valve located in said air conduit in said neck of said handle to allow air to flow only from said air conduit to said cavity.

21. The dental apparatus of claim 20, further comprising;

a nozzle integrally coupled to said neck of said handle and extending away from said handle, said nozzle having a passage extending therethrough from a nozzle end through said neck of said handle, said nozzle end having a nozzle aperture extending therethrough and communicating with said passage;

said housing of said head assembly having a nozzle receptacle extending therein, said nozzle being removably located in said nozzle receptacle wherein said housing has a housing aperture extending therethrough close to said burr, said nozzle aperture being located close to said housing aperture when said nozzle is located in said nozzle receptacle;

a water conduit, said water conduit extending through said handle into said passage in said nozzle and extending through said passage to said nozzle end, said water conduit being located in said passage at said nozzle end to dispense water from a water source through said nozzle and housing apertures;

said air conduit is defined as a first air conduit;

a second air conduit, said second air conduit extending through said handle into said passage in said nozzle and extending through said passage to said nozzle end, said second air conduit being located in said passage at said nozzle end to direct air from an air source through said nozzle and housing apertures;

fiber optic means extending into said handle and into said passage in said nozzle and extending through said passage to said nozzle end, said fiber optic means being located in said passage close to said nozzle and housing apertures, said fiber optic means being capable of illuminating said burr through said nozzle and housing apertures.

22. The dental apparatus of claim 21, further comprising:

a plurality of bearings located in said housing for supporting said turbine and for rotation.

23. A handle to be removably coupled to a head assembly of a dental drill of the type having a turbine coupled to a shaft located in a cavity wherein a drill burr may be coupled to the shaft at one end of the head assembly, comprising:

a body having a forward end and an opposite rear end such that said forward end may be removably coupled to the head assembly, said body having an air inlet passage and an air outlet passage at said forward end for use for directing and removing air to and from the turbine for rotating the turbine, said body having a light conduit and a fluid conduit at said forward end for use for directing light and fluid toward the drill burr, said body having a top portion, a bottom portion and two opposite sides, said body comprising a proboscis member extending forward from a forward facing wall at said forward end of said body with said wall being located at said top portion of said body with said inlet and outlet passages extending through said wall above said proboscis member, said light and fluid conduits extending through first and second orifices respectively at the forward end of said proboscis member at said bottom portion of said body at positions forward of said wall.

24. The handle of claim 23, wherein:

said body in cross section near and rearward of said wall has a generally triangular shape with said top portion being generally flattened and said bottom portion being generally pointed.

25. The handle of claim 23, comprising:

the forward portion of said light conduit is curved, a light pipe located in said light conduit and having a forward end located rearward of said first orifice and rearward of said curved portion of said light conduit, said light conduit forward of said forward end of said light pipe providing high reflectivity to allow light exiting said light pipe to pass out of said light conduit through said first orifice.

26. The handle of claim 23, comprising:

the forward portion of said light conduit is curved, a light pipe located in said light conduit and having a forward end located rearward of said first orifice and rearward of said curved portion of said light conduit, a lens located in said curved portion of said light conduit between said forward end of said light pipe and said first orifice for providing a reflective path to allow light exiting said light pipe to pass out of said first orifice of said light conduit.

27. A disposable head assembly and a handle for a dental drill, comprising:

a housing forming a head with first and second opposite ends and a neck extending from a side of said head between said first and second opposite ends to a coupling end, a head cavity formed in said head with first and second openings at said first and second ends respectively leading to said head cavity, a shaft having first and second ends, a turbine coupled to said shaft between said first and second ends of said shaft with said second end being adapted to have a drill burr coupled thereto, first and second bearing means located in said cavity for supporting said shaft and said turbine, for rotation, an air inlet channel and an air outlet channel extending from said coupling end of said neck and leading to said head cavity for directing air onto said turbine and from said head cavity for rotating said turbine; and a neck cavity extending from said coupling end of said neck to an outlet opening located close to and directed toward said drill burr when extending out of said second opening of said second end of said head;

said neck cavity being adapted to receive the proboscis of a handle to be located next to said outlet opening of said neck cavity;

said neck cavity having a cross-sectional area at said coupling end of said substantially greater than that of either of said air inlet channel and said air outlet channel.

28. The disposable head assembly of claim 27, wherein:

said air and inlet channels are located side by side and;

said neck has a top portion, a bottom portion and two opposite sides;

said air and inlet channels are located in said top portion of said neck and said neck cavity is located in said bottom portion of said neck, the cross-sectional area of said neck cavity decreases in size from said coupling and toward said outlet opening of said neck cavity.

* * * * *